(12) United States Patent
Audière et al.

(10) Patent No.: US 12,053,328 B2
(45) Date of Patent: Aug. 6, 2024

(54) ELASTOGRAPHY DEVICE AND METHOD

(71) Applicant: ECHOSENS, Paris (FR)

(72) Inventors: Stéphane Audière, Paris (FR); Cécile Bastard, Paris (FR); Hugo Lorée, Nogent-sur-Marne (FR); Véronique Miette, L'Hay-les-Roses (FR); Laurent Sandrin, Bourg-la-Reine (FR)

(73) Assignee: ECHOSENS, Paris (FR)

( * ) Notice: Subject to any disclaimer, the term of this patent is extended or adjusted under 35 U.S.C. 154(b) by 3 days.

(21) Appl. No.: 17/695,053

(22) Filed: Mar. 15, 2022

(65) Prior Publication Data

US 2023/0293154 A1  Sep. 21, 2023

(51) Int. Cl.
*A61B 8/00* (2006.01)
*A61B 8/08* (2006.01)
*A61B 8/14* (2006.01)

(52) U.S. Cl.
CPC .................. *A61B 8/54* (2013.01); *A61B 8/08* (2013.01); *A61B 8/14* (2013.01); *A61B 8/4254* (2013.01); *A61B 8/461* (2013.01); *A61B 8/5207* (2013.01); *A61B 8/5223* (2013.01)

(58) Field of Classification Search
CPC .... A61B 8/54; A61B 8/08; A61B 8/14; A61B 8/4254; A61B 8/461; A61B 8/5207; A61B 8/5223
See application file for complete search history.

(56) References Cited

U.S. PATENT DOCUMENTS

| 9,636,085 | B2 | 5/2017 | Sandrin et al. | |
| 2015/0057542 | A1* | 2/2015 | Katsuyama | A61B 8/085 600/438 |
| 2015/0141822 | A1* | 5/2015 | Miyauchi | A61B 8/5223 600/438 |
| 2016/0249883 | A1* | 9/2016 | Lee | A61B 8/4472 600/438 |
| 2020/0390421 | A1 | 12/2020 | Audière et al. | |

(Continued)

OTHER PUBLICATIONS

Extended European Search Report as issued in European Patent Application No. 22305298.6, dated Aug. 22, 2022.

(Continued)

*Primary Examiner* — Baisakhi Roy
*Assistant Examiner* — Kaitlyn E Sebastian
(74) *Attorney, Agent, or Firm* — Pillsbury Winthrop Shaw Pittman LLP

(57) ABSTRACT

An elastography device comprising: a probe that comprises a protruding part to be applied against the body of a subject, a low frequency vibrator arranged to move the protruding part, at least one ultrasound emitter and one ultrasound receiver; and an electronic unit. The electronic unit is adapted to alternatively control the elastography device so that it operates (a) in a guidance mode to determine whether the probe is correctly positioned in front of a region of the body to be probed to carry out a measurement of a mechanical property of the probed region and (b) in a measurement. In the guidance mode, the vibrator delivers a plurality of successive probing pulses (PRB), each being a transient, low frequency mechanical pulse, and the electronic unit determines a propagation quality indicator (Q) representative of an aptitude of the probed region to transmit the probing pulse.

18 Claims, 11 Drawing Sheets

(56) References Cited

U.S. PATENT DOCUMENTS

2021/0022709 A1\* 1/2021 Sandrin ............... G01S 7/52041
2021/0052250 A1\* 2/2021 Sandrin ................. A61B 8/085

OTHER PUBLICATIONS

Lorée, H., et al., "Vibration-Guided Transient Elastography: A Novel Fibroscan® Examination With Improved Guidance for Liver Stiffness Measurement," Ultrasound in Medicine and Biology, vol. 46, No. 9, Jun. 2020, pp. 2193-2206.
Sandrin, L., et al., "The role of the coupling term in transient elastography." J. Acoust. Soc. Am., vol. 115, No. 1, Jan. 2004, pp. 73-83.

\* cited by examiner

ELASTOGRAPHY DEVICE AND METHOD

FIELD

The disclosed technology concerns an elastography device and method. It concerns more particularly an elastography device comprising a probe that comprises: a low frequency vibrator, to deliver low frequency mechanical pulses to the body of a subject; and at least one ultrasound emitter and one ultrasound receiver arranged to emit ultrasound pulses and to receive corresponding echoes to track how the low frequency mechanical pulses travel in the body of the subject, in order to characterize tissue stiffness in the region of the body of the subject thus examined.

BACKGROUND

Liver stiffness, measured for instance by Vibration-Controlled Transient Elastography (herein after VCTE), has been shown to be a very useful tool to help health care professionals to detect or to characterize liver disease or damages, and more generally to monitor the condition of the liver of a subject.

A well known transient elastography system is the FIBROSCAN® system (an ultrasound-based elastography apparatus for measuring the stiffness (or elasticity) and ultrasound attenuation of tissues and organs), produced and sold by Echosens SA of Paris, France, which enables an operator to non-invasively measure liver or other organs stiffness to assess the organ's health.

With the FIBROSCAN® system, an operator places the tip of a probe, that has a rather small diameter (typically comprised between 5 and 10 mm), in contact with the subject's body, in front of the expected area of a subject's liver. The operator then presses a button to make the probe's head deliver to the subject a transient, low frequency mechanical pulse (the spectrum of this pulse is centered on a frequency comprised typically between 10 and 500 hertz). This pulse generates an elastic wave that travels in the subject's body. An ultrasound transducer mounted on the probe's tip, in contact with the subject's body, then emits a number of ultrasound shots into the tissue, with a high repetition rate, of 6 kilohertz for instance. The echo signals, corresponding to the backscattering of the different ultrasound shots emitted, are acquired by the probe to track slight movements of the tissue caused by the elastic wave passing through. The tracking is performed using correlation techniques applied to successive echo signals. The detected movements enable one to compound an elastic wave propagation image showing the tissue deformation both as a function of depth z, and as a function of time t, sometimes referred to as an "elastogram" (FIG. 1).

The mechanical pulse delivered by the FIBROSCAN® probe's tip generates both a shear wave and of a compression wave. In other words, the elastic wave mentioned above combines a shear wave and a compression wave. But these two waves have very different propagation speeds and, thanks to the transient nature of the mechanical excitation, they can be easily separated in time and identified in the elastic wave propagation image. For example, referring to FIG. 1, this figure shows an elastic wave propagation image 105. In FIG. 1, the compression wave is identified by the reference sign 105C, while the much slower shear wave is identified by the reference sign 105S. Also shown in FIG. 1, is a region of interest (ROI) which is bound by two dashed lines at 25 mm and 65 mm, which corresponds to the depth under the patient skin where liver is typically located. This elastic wave propagation image can thus be used to precisely determine the propagation speed of shear waves in the tissue to be characterized, from which the stiffness of this tissue can be derived. These stiffness results are then provided to the operator.

While the FIBROSCAN® technology works well, it is sometimes difficult for an operator to know if he has correctly positioned the probe, in front of an area of homogeneous liver tissue, or if he is even aiming the probe at the liver at all. Ribs in front of the liver, blood vessels, liquid pockets (ascites) or other artifacts of non-homogeneous tissue such a cysts or tumors in the liver tissue can produce erroneous measurements of both tissue stiffness and ultrasound attenuation. In addition, an operator may believe that he/she is aiming the probe at the liver, when in fact the probe is too close to the lungs or other internal organs. As a result, the system may not be able to obtain accurate measurements.

Document US2021022709, which is a patent application assigned to the applicant, describes a method for helping the operator of such a transient elastography device to find an adequate probe position. According to this method, the vibrator of the probe first delivers a continuous and periodic mechanical vibration, for instance a sinusoidal vibration, to probe the region of the body of the subject toward which the probe is directed. Ultrasound pulses are emitted, and corresponding echoes signals are acquired to track how this sinusoidal vibration travels through the probed region. A "harmonic elastogram", representing the periodic deformation of the tissue caused by this vibration as a function of time t and depth z, is then computed and displayed. It shows how this sinusoidal vibration travels in the region in question. A harmonic elastogram in which a rather well defined diagonal stripe or stripes can be distinguished, such as the one of FIG. 16 of US2021022709, indicates that the medium in front of the probe is homogeneous (with respect to the propagation of elastic waves), and that the probe is thus probably well positioned. On the contrary, a harmonic elastogram showing disordered propagation, in which no diagonal stripe can be distinguished (such as the one of FIG. 17 of US2021022709) indicates that the probe is not adequately positioned. Exerting this harmonic vibration on the body of the subject, and visualizing the corresponding tissue strain (using ultrasound echoes correlations), thus helps the operator finding an adequate position and direction for the probe. Once such a position is found, the operator triggers a transient Vibration-Controlled Transient Elastography measurement such as described above.

The periodic-vibration guidance method described in US2021022709 improves substantially the operability of a VCTE system like the FIBROSCAN® (compared to conventional guidance based on A-mode and M-mode ultrasound imaging) and provides satisfactory guidance. In particular, due to the continuous nature of the vibration, there is no unpleasant feeling for the subject under examination, and the guidance may be continuous.

Still, the inventors have observed that, in some situations, the guidance information obtained in this way, by harmonic-vibration probing leads the conclusion that the probe is not adequately positioned while a good quality transient-vibration elastography measurement could in fact be carried on.

SUMMARY

In this context, the disclosed technology is directed to an elastography device comprising:
    a probe that comprises: a protruding part to be applied against the body of a subject, a low frequency vibrator arranged to move the protruding part of the probe, at least one ultrasound emitter and one ultrasound receiver; and an electronic unit comprising electronic circuitry adapted to alternatively control the elastography device so that it operates (a) in a guidance mode to determine whether the probe is correctly positioned in front of a region of the body to be probed to carry out a measurement of a mechanical property of the probed region and (b) in a measurement mode to carry out said measurement, the electronic circuitry being adapted to execute the following procedure:

during the guidance mode, the electronic unit controls the low frequency vibrator (5) to deliver to the body of the subject, successively and repeatedly, a plurality of probing pulses, each probing pulse being a transient, low frequency mechanical pulse, for each probing pulse, the electronic unit controls the ultrasound emitter to emit a sequence of ultrasound pulses, and acquires echo signals received in response by the ultrasound receiver to track how the probing pulse propagates through the probed region of the body of the subject, located in front of the protruding part of the probe, the electronic unit determines, from at least some of said echo signals, a propagation quality indicator representative of an aptitude of the probed region to transmit the probing pulse and representative of a homogeneity of the probed region with respect to the propagation of the probing pulse, the electronic unit controls the elastography device to transmit guidance information, the guidance information being based on the propagation quality indicator, during the measurement mode, the electronic unit controls the low frequency vibrator to deliver to the probed region a measurement pulse, the measurement pulse being a transient low frequency mechanical pulse having an amplitude higher than an amplitude of each of the plurality of probing pulses, the electronic unit controls the ultrasound emitter to emit a sequence of ultrasound pulses, and acquires echo signals received in response by the ultrasound receiver to track how the measurement pulse propagates through the probed region, and the electronic unit determines, from at least some of said echo signals, said mechanical property, said mechanical property being related to low frequency elastic wave propagation.

With this device, when it is operating in the guidance mode, the region located in front of the probe is probed by reduced-amplitude transient mechanical pulses, repeated several times (instead of a harmonic vibration). When in the guidance mode, the body of the subject is thus probed in conditions that are close to the ones under which the final transient measurement itself is carried on. The guidance information obtained thanks to this device thus prefigures accurately the quality of the measurement that can be obtained, for the position of the probe considered, and thus constitutes very useful guidance information.

In particular, this transient-pulses based guidance resembles more the measurement itself than a harmonic-vibration based guidance, and thus enables a better guidance.

Harmonic-vibration based guidance has some benefits (in particular, it may be easier to implement than transient-pulses based guidance), but the guidance "harmonic elastograms" thus obtained can be skewed by elastic wave reflections inside the tissue, which may create stationary waves patterns, like the one shown in FIG. 2.

In some situations, this sensitivity to reflections is useful (to detect the presence of a vessel on the probe axis, for instance). But in other situations, this high sensitivity to reflections (enhanced by the continuous, repeated nature of the vibration, with no downtime) leads to degraded "harmonic elastograms" while the probe positioning would in fact enables a good quality transient measurement. This happens for instance when the probe axis passes close to an edge of the liver of the subject (see FIGS. 4 and 5). In such a case, the proximity of the liver boundaries creates stationary-wave pattern that degrades the "harmonic elastograms" while good transient elastograms could be obtained.

This is illustrated by FIGS. 2 and 3. FIG. 2 shows a harmonic elastogram obtained by applying a 25 Hz harmonic vibration to a phantom (a synthetized elastic medium whose mechanical properties are close to those of liver), with the probe tip positioned close to a sidewall of the phantom. FIG. 3 shows an elastogram obtained by applying a transient vibration, comprising of a single period of a 25 Hz sinusoid, to the same phantom, the probe's positioning being identical as for FIG. 2. The ultrasound pulses repetition rate is 2 kHz for both acquisitions. The comparison of FIGS. 2 and 3 clearly shows that transient-pulses guidance leads to an adequate-positioning detection that is more sensitive than with a harmonic-vibration based guidance.

The probing pulses delivered when the device operates in the guidance mode may be used also to carry on a kind of pre-measurement of the mechanical property of interest, typically of the tissue stiffness (for instance for each probing pulse). This preliminary estimate of the tissue stiffness may help the operator positioning the probe (a preliminary stiffness value belonging to given interval confirming that the probe is probably positioned in front of liver, for instance). And a pre-measurement of tissue stiffness carried on with a transient mechanical pulse is generally more accurate than one carried on with a periodic mechanical vibration with no rest-period (even if the "harmonic elastogram" is of high quality). Indeed, with a periodic mechanical vibration, a mixing occurs between shear waves and compression waves, in the medium to be characterized (due to the repetitive, restless nature of the vibration), and the elastic wave observed in a harmonic elastogram mixes shear waves and compression waves, whose propagation speeds are very different, thus leading to a biased estimation of the tissue stiffness. So, transient-pulses based guidance enables a more accurate pre-estimation of the tissue stiffness than harmonic-vibration based guidance.

With the disclosed device, thanks to the transient nature of each probing pulse, the value of a propagation quality indicator determined for a given probing pulse corresponds precisely, from a temporal point of view, to this probing pulse (with no mixing between successive periods of a periodic vibration). The propagation quality indicator is representative of the aptitude of a region to transmit the probing pulses and of its homogeneity with respect to this propagation. With this transient-pulses guidance method, the temporal monitoring of the propagation quality (and, possibly, of the pre-estimates of the tissue stiffness) is thus more accurate than with a harmonic, continuous vibration.

Besides, as the probing pulses are transient, with a downtime between each other, the ultrasound pulses, emitted to track how they travel, may be emitted during a fraction only of the total duration during which the guidance mode is employed, which reduces the overall quantity of ultrasound emitted and therefore the overall average acoustic power delivered to the patient.

Besides, as the probing pulses are transient, with a downtime between each other, the low frequency vibrator requires less power and the amplifier that drives will experience less heating and therefore require less dissipation means.

By transient pulse, it is meant a mechanical vibration that is temporary. The duration of the pulse, that is the active time, during which there is a substantial motion protruding part (induced by the vibrator) is followed by a downtime during which there is no or substantially no motion of the protruding part. By substantially no motion, it is meant for instance that, during this downtime, the displacement of the protruding part that may be induced by the vibrator remains smaller than 1/10 or even 1/20 of the peak displacement of protruding part. For the transient pulses mentioned above (either the probing pulses, or the measurement pulse), an actuation ratio, equal to the pulse's active time, divided by the sum of this active time and the following down time, is typically below 50%, or even below 20%. The downtime in question is the duration between the end of the active time and a subsequent significant motion of the protruding part (corresponding for instance to a subsequent transient, probing pulse), should there be any.

By low frequency pulse, it is meant that the central frequency of the pulse is below 500 Hz, or even below 250 Hz. The central frequency of the pulse is, for instance, the average or the median frequency of the spectrum of the displacement or of the speed of displacement corresponding to that pulse, or the peak frequency of a main peak of this spectrum, or the mean of the −3 dB or −6 dB cutoff frequencies of the spectrum.

In the elastography device according to the instant technology, the electronic unit may be configured to control the vibrator so that, in the guidance mode, for at least some of the plurality of probing pulses, a central frequency of the probing pulse is lower than a central frequency of the measurement pulse delivered in the measurement mode. For instance, the central frequency of these probing pulses may be at least 5%, or even 10 or 20% lower (or possibly, at least 50% lower) than the centrale frequency of the measurement pulse.

The device may in particular be configured for characterizing liver, the electronic unit being configured to control the vibrator so that, in the guidance mode, for at least some of the plurality of probing pulses, the central frequency of the probing pulse is between 20 Hz and 45 Hz while in the measurement mode, the central frequency of the measurement pulse is between 50 Hz and 200 Hz, for example. As an example, the central frequency of each probing pulse may be 40 or 45 Hz while the central frequency of the measurement pulse is 50 Hz.

The device may also be configured for characterizing spleen, the electronic unit being configured to control the vibrator so that, in the guidance mode, for at least some of the plurality of probing pulses, the central frequency of the probing pulse is between 20 Hz and 90 Hz while in the measurement mode the central frequency of the measurement pulse is between 100 Hz and 200 Hz. As an example, the central frequency of each probing pulse may be 80 Hz while the central frequency of the measurement pulse is 100 Hz.

Reducing the central frequency of the probing pulses enables these pulses to propagate deeper in the medium to be probed Indeed, the propagation depth increases as the frequency decreases, in visco-elastic mediums like liver or analogous mediums. Increasing the propagation depth of the probing pulses is beneficial as it enables to compensate for their low amplitude, which is intentionally limited so that these probing pulses, frequently repeated, are not uncomfortable for the subject under examination.

Besides, reducing the central frequency of the probing pulses contributes to the non-uncomfortable nature of the probing pulses. Indeed, the strength of the pulse experienced by the subject depends both on the pulse amplitude and on the pulse central frequency (as the speed of displacement, and even the acceleration experienced by the subject depends both on the pulse amplitude and on its frequency).

It may be noted that, a very low frequency is, on the contrary, not desirable for the measurement pulse. Indeed, when the frequency decreases, the wavelength increases and diffraction effects increase too. And the presence of diffraction effects increases the apparent shear wave speed values and, in turn, induces overestimations of stiffness, which is not favorable for diagnosis purposes, as explained in the following article: "The role of the coupling term in transient elastography." By Sandrin, L., D. Cassereau and M. Fink, (2004), J Acoust Soc Am 115(1): 73-83. So, regarding the measurement itself, it is not desirable to use a low or very low frequency. For the probing pulses, the (pre)measurement accuracy is reduced as well, when using very low frequency probing pulses, but this reduction of accuracy does not matter a lot as the probing pulses are usually not employed for obtaining the final value of the mechanical property of the tissue (value, such as the tissue stiffness, which may be employed to characterize the condition of the tissue). And so, it is finally desirable, for the probing pulses, to use a central frequency lower than that of the measurement pulse, to take advantage of the benefits (mentioned in the paragraphs above) of such a low probing frequency.

Regarding the amplitude of the probing pulses, in the guidance mode, for at least some of the plurality of probing pulses, an amplitude of displacement of the protruding part of the probe may be at least 10 or 20% lower, or even 50% lower or below than an amplitude of displacement of the protruding part during the measurement pulse delivered in said measurement mode. The peak-to-peak amplitude of the displacement of the protruding part of the probe may be between 1 and 4 mm for the measurement pulse, for instance. And it may be between 0.1 and 2 mm for at least some of the probing pulses.

In the elastography device according to the instant technology, the electronic unit may be configured also to control the ultrasound emitter so that, in the guidance mode, for at least some of the plurality of probing pulses, a repetition rate with which the ultrasound pulses are emitted, to track how the probing pulse propagates, is lower (for instance, at least 20% lower, and possibly at least two or three times lower) than a repetition rate of the ultrasound pulses that are emitted during the measurement mode to track how the measurement pulse propagates.

For instance, the measurement pulse may be tracked with an ultrasound pulses repetition rate between 2 and 10 kHz. While the probing pulses are each tracked with an ultrasound pulses repetition rate between 0.5 and 2 kHz, or even between 0.5 and 3 kHz. For example, an ultrasound (hereinafter U/S) pulse repetition rate of 6 kHz may be used to track the measurement pulse, when characterizing liver (or, alternatively, a rate of 8 kHz, for spleen), while an U/S pulse repetition rate of 1, 2 or 3 kHz could be used to track each probing pulse.

Reducing the ultrasound pulses repetition rate for the probing pulses (which themselves are repeated often, typically several times per seconds) enables to reduce the overall acoustic output power emitted by the elastography device and to reduce the computation time. It is beneficial as the total number of ultrasound pulses will be lower to cover the same duration which will eventually reduce the number of lines that need to be processed, when in the guidance mode. It is also beneficial, as it reduces the amount of acoustic output power to which the patient is exposed during the examination and helps fulfilling regulations regarding ultrasound radiations by electronic devices (such as those specified by the IEC 60601-2-37 standard on diagnostic ultrasound devices). Reducing the acoustic output power is important for the device to be used by operators without specific ultrasound imaging certifications. In this respect, it may be noted that a high ultrasound pulses repetition rate is not essential for tracking the probing pulses, as a smaller temporal and spatial resolution is not required for these pulses, compared to the measurement pulse itself. Besides, the central frequency of the probing pulses is typically lower than that of the measurement pulse, and so, a lower ultrasound pulses repetition rate can be employed to track them (without necessarily reducing the tracking resolution). As a matter of fact, given that the amplitude of the probing pulses is lower, having a larger time difference in-between successive ultrasound pulses is favorable to let the tissue experience a displacement that is sufficient to be measured between successive ultrasound pulses using correlation techniques. To reduce the overall acoustic output power emitted by the elastography device, the U/S pulses emitted when in guidance mode may have a different shape (more favorable regarding the acoustic power radiated) than the one emitted when using the measurement mode.

In the elastography device according to the instant technology, the electronic unit may be configured to control the vibrator so that, in the guidance mode, the probing pulses are delivered with a rate of several pulses per second, for instance more than five probing pulses per second (in practice, a rate of typically 10 pulses per second is well suited, for such a guidance).

This enables an almost continuous guidance, for the operator.

The electronic unit may be configured also, in the guidance mode, for at least some of the plurality of probing pulses, a time lag between the transmission of the probing pulse to the body of the subject, and a transmission of the corresponding guidance information, is below 0.5 second or even below 0.3 or 0.2 second, and/or is below a repetition period with which the probing pulses are repeated.

The operator is thus guided almost continuously, and in real time, when in the guidance mode.

Thanks to the various features presented above, this transient-pulses guidance does not suffer from discomfort or discontinuous guidance drawbacks that could be expected at first glance, and provides numerous improvements compared to the prior art.

Still, it may be noted that such a real-time guidance, based on transient probing pulses, is very challenging from a computational point of view, as it requires on the flight processing of each series of echoes, or, in other words, on the flight determination of an elastogram, for each probing pulse, several times per second.

To achieve this, the electronic unit may for instance comprise two processors:
 a first, special purpose processor, like an FPGA ("Field Programmable Gate Array"), for processing the echo signals acquired using a correlation technique, to determine tissue strain, or, more generally, a tissue motion parameter, (as a function of time and depth), and
 a second, general-purpose processor.

This architecture accelerates notably the processing of the echo signals, in particular because the (pre)processing achieved by the first processor reduces substantially (typically by a factor of 10, or even more) the quantity of data to be transmitted to the general-purpose processor, thus reducing the corresponding transmission time. And in practice, this transmission time is often the most time limiting step of the overall processing of the echo signals.

Still, implementing the correlation technique in question in such a special purpose processor is challenging in itself. Indeed, the displacement of the probe's tip or head is desirably compensated before correlating the echo signals with each other, and the usual techniques to compensate for this displacement (based on strong echo detection, and Fourier-domain compensation) are not easy, or even impossible to implemented in such a special-purpose processor. To achieve such a displacement compensation, the ultrasound pulses emission and/or reception times may for instance be pre-compensated (upon emission and/or reception), depending on the probe's tip or head displacement, as explained in the not-yet published US patent application U.S. Ser. No. 17/371,790 assigned to the applicant.

The applicant thus underlines that implementing in real time the transient-pulses based guidance method presented above may require specific development efforts and does not correspond to a mere adjustment of working parameters.

The acceleration of the processing of the ultrasound signals mentioned above allows to average the tissue strain for several successive probing (or measurement) pulses in order to improve the signal to noise ratio (SNR) of the elastogram (as this acceleration allows for determining several elastograms per seconds). This can be used for display purposes, for example, when in the guidance mode. For instance, the probing pulses may be repeated with a rate of 10 pulses per second (or more), and an averaged elastogram, corresponding to a rolling average computed by averaging 3, 4 or 5 successive elastograms (corresponding respectively to 3, 4 or 5 successive probing pulses), may be displayed.

This can also be used for measurement purposes. Indeed, when performing the measurement pulses, several times, very rapidly, the medium cannot move significantly (relative to the probe, or relative to other organs of the subject) in between the pulses which allows for averaging and therefore improving the signal to noise ratio for this measurement. For example, four measurement pulses can be performed at a rate of 10 pulses per second. The measurement pulses are therefore performed in less than 400 ms. Each measurement pulse is processed in order to retrieve an elastogram. The algorithm for shear wave speed estimation is applied on the sum or mean of the four elastograms. Another possibility would be, for instance, to perform four measurements per second for several seconds in order to accumulate a large number of measurements. It allows to perform advanced statistics (other than median) on the measured values (detection of Gaussian on the distribution for example).

In this respect, the electronic unit may be configured so that, when in the device is operated in the measurement mode:
the electronic unit controls the vibrator to deliver to the body of the subject, in addition to the measurement pulse, one or more subsequent, additional measurement pulses, each being a transient low frequency mechanical pulse,
for each measurement pulse, the electronic unit determines tissue strain data within the probed region, from echo signals acquired to track how each measurement pulse propagates through the probed region,
the electronic unit determines the mechanical property related to low frequency elastic wave propagation by averaging, taking into account the tissue strain data associated respectively to the different measurement pulses delivered to the body of the subject.

The electronic unit may be configured, so that, in the guidance mode, for each of the plurality of probing pulses:
the electronic unit determines tissue strain data, representative of tissue strain within the probed region as a function of time and as a function of depth within the probed region, the tissue strain data being determined from at least some of the echo signals acquired to track how the probing pulse propagates through the probed region.

The electronic unit may then determine the propagation quality indicator based on the tissue strain data.

The tissue strain data mentioned above may gather, for different values of depth and time, the tissue strain itself (that is, its relative extension), or a displacement of the tissue at the position considered, or a strain rate, or a time derivative or integral of one of these quantities, or any other equivalent quantity; More generally, it is a tissue motion parameter, representative of the motion of the tissue at the time and depth considered. Besides, in this document, by "elastogram", it is meant any representation of such a motion parameter, as a function of depth and time.

It may be noted that, in some embodiments, the propagation quality indicator can be a graphical representation of the tissue strain.

The guidance information may correspond directly to the propagation quality indicator itself. It may also correspond to an indicator derived from the propagation quality indicator; for instance, the guidance information may take the form of a binary (for instance red/green) indicator, whose value specifies whether the propagation quality indicator is above or below a given quality threshold.

The guidance information may also take into account, or represent one or more other parameters, in addition to the propagation quality indicator. For instance, the guidance information may combine the propagation quality indicator and an ultrasound-based guiding information. The ultrasound-based guiding information may be determined from the ultrasound echo signals, so as to be representative of the more or less homogeneous nature of the region located in front of the probe with respect to U/S propagation and/or to be representative of the fact that the U/S attenuation in this region is within an attenuation range expected for the organ to be characterized. The ultrasound-based guiding information may be determined, for instance, based on the coefficient of determination ($R^2$) of a linear regression applied to an envelope of the U/S echo signals (this criteria being all the higher as the coefficient of determination is close to 1). It may also be determined so as to specify whether an U/S attenuation value is within an expected range, for example in the 100-400 dB/m range (when the organ to be characterized is liver), as explained in the US patent application published as US2020390421, or in the US patent U.S. Pat. No. 9,636,085.

The guidance information may be transmitted by a visual transmission device, such as a display, a Light-Emitting Diode or LED (for instance, a color LED) or a set of LEDS, the visual transmission device being arranged on the probe. This enables the operator to access the guidance information while remaining focused on the probe he is holding and positioning on the subject's body. In particular, the electronic unit may be configured to turn on the LED or LEDs mentioned above, as a function of the propagation quality criteria, to inform the operator and allowing the operator to stay focused on the probe.

The elastography device presented above may also comprise one or more of the following complementary and non-limiting features, considered individually or according to all technically possible combinations:
in the guidance mode, for each of the plurality of probing pulses:
the electronic unit determines a probing pulse time of flight, as a function of depth within the probed region, the probing pulse time of flight being determined from the tissue strain data, and
the electronic unit determines the propagation quality indicator (Q) so that it specifies whether the probing pulse time of flight varies linearly and smoothly and with depth, or not;
in said guidance mode, the electronic unit is configured to compute averaged tissue strain data by averaging the tissue strain data corresponding respectively to several of the plurality of probing pulses;
in said guidance mode, the electronic unit is configured to control a display device to display an averaged elastogram representing the averaged tissue strain data as a function of time and depth;
the electronic unit is configured so that, in said measurement mode:
electronic unit controls the vibrator to deliver to the body of the subject, in addition to said measurement pulse, one or more subsequent, additional measurement pulses, each being a transient low frequency mechanical pulse,
for each measurement pulse, the electronic unit determines tissue strain data within the probed region, from echo signals acquired to track how each measurement pulse propagates through the probed region,
the electronic unit determines said mechanical property related to low frequency elastic wave propagation by averaging, taking into account the tissue strain data associated respectively to the different measurement pulses delivered to the body of the subject;
the electronic unit is configured to adjust a central frequency of the measurement pulse to be delivered to the body of the subject, based on a property of the probed region of the body of the subject probed by at least one of the plurality of probing pulses;
said property is representative of an attenuation underwent by the probing pulse during its propagation within said probed region, and wherein the electronic unit is configured to adjust the central frequency of the measurement pulse so that it is all the higher as the attenuation in the region is high;

the electronic unit is configured:
- to control the vibrator so that, during the guidance mode, at least some of the plurality of probing pulses are each followed:
  - by a time lapse with substantially no displacement of the protruding part of the probe,
  - and then by a periodic mechanical vibration, comprising of a same vibration pattern repeated several times successively overtime, with substantially no downtime of the vibrator during the periodic mechanical vibration,
- to emit a sequence of ultrasound pulses and to acquire echo signals received in response, to track how the periodic mechanical vibration propagates through the probed region of the body of the subject, located in front of the protruding part of the probe, and to determine a periodic-vibration propagation quality level, from at least some of these echo signals,
- to determine an edge-proximity indicator based on a comparison of the periodic-vibration propagation quality level with the propagation quality indicator, and to transmit the edge-proximity indicator.

The instant technology concerns also an elastography method,
implemented by an elastography device that includes a probe including a protruding part to be applied against the body of a subject, a low frequency vibrator arranged to move the protruding part of the probe, at least one ultrasound emitter and one ultrasound receiver; and an electronic unit, comprising electronic circuitry adapted to alternatively control the elastography device so that it operates (a) in a guidance mode to determine whether the probe is correctly positioned in front of a region of the body to be probed to carry out a measurement of a mechanical property of the probed region and (b) in a measurement mode to carry out said measurement,
the method comprising:
- carrying out the guidance mode, the guidance mode including:
  - controlling, by the electronic unit, the vibrator to deliver to the body of the subject, successively and repeatedly, a plurality of probing pulses, each probing pulse being a transient, low frequency mechanical pulse,
  - for each probing pulse,
    - controlling, by the electronic unit, the ultrasound emitter to emit a sequence of ultrasound pulses, and acquiring, by the ultrasound receiver, echo signals to track how the probing pulse propagates through the probed region of the body of the subject located in front of the protruding part of the probe,
    - determining, by the electronic unit, from at least some of said echo signals, a propagation quality indicator representative of an aptitude of the probed region to transmit the probing pulse and representative of a homogeneity of the probed region with respect to the propagation of the probing pulse,
  - transmitting guidance information, the guidance information being based on the propagation quality indicator, and then,
- carrying out the measurement mode, the measurement mode including:
  - controlling, by the electronic unit, the vibrator, to deliver to the body of the subject a measurement pulse, the measurement pulse being a transient low frequency mechanical pulse having an amplitude higher than an amplitude of each of the plurality of probing pulses,
  - controlling, by the electronic unit, the ultrasound emitter to emit a sequence of ultrasound pulses, and acquiring, by the ultrasound receiver, echo signals to track how the measurement pulse propagates through the probed region of the body of the subject located in front of the protruding part of the probe, and
  - determining, by the electronic unit, from at least some of said echo signals, the mechanical property of said region of the body of the subject, related to low frequency elastic wave propagation.

The different features of the elastography device presented above may apply also to this elastography method.

DETAILED DESCRIPTION

As mentioned above, the instant technology concerns an elastography device configured to generate elastic waves, propagating in a medium to be explored, by moving an element which is in contact with the surface of the medium, such as a probe tip (or, more generally, a protruding part of a probe of the device), and to track how the elastic wave travels in the medium (or, in other words, how the medium is moved by the vibration exerted upon it), by transmitting ultrasound pulses in the medium, and recording echo signals received in response. The instant technology concerns in particular such an elastography device having special guidance features to help an operator of the device to easily find an adequate probe's position.

This guidance is achieved by delivering to the body of the subject, successively and repeatedly, a plurality of probing pulses, each probing pulse being a transient, low frequency mechanical pulse (of low amplitude) that enables to test an aptitude of the region, located in a front region of the probe, to transmit transient pulses, and to test a homogeneity of this region with respect to the propagation of such transient pulses. Employing such transient probing pulses enable to probe the body of the subject under conditions close to the ones corresponding to an actual Vibration-Controled-Transient-Elastography measurement, thus leading to a well-adapted positioning of the probe.

Figure 6:
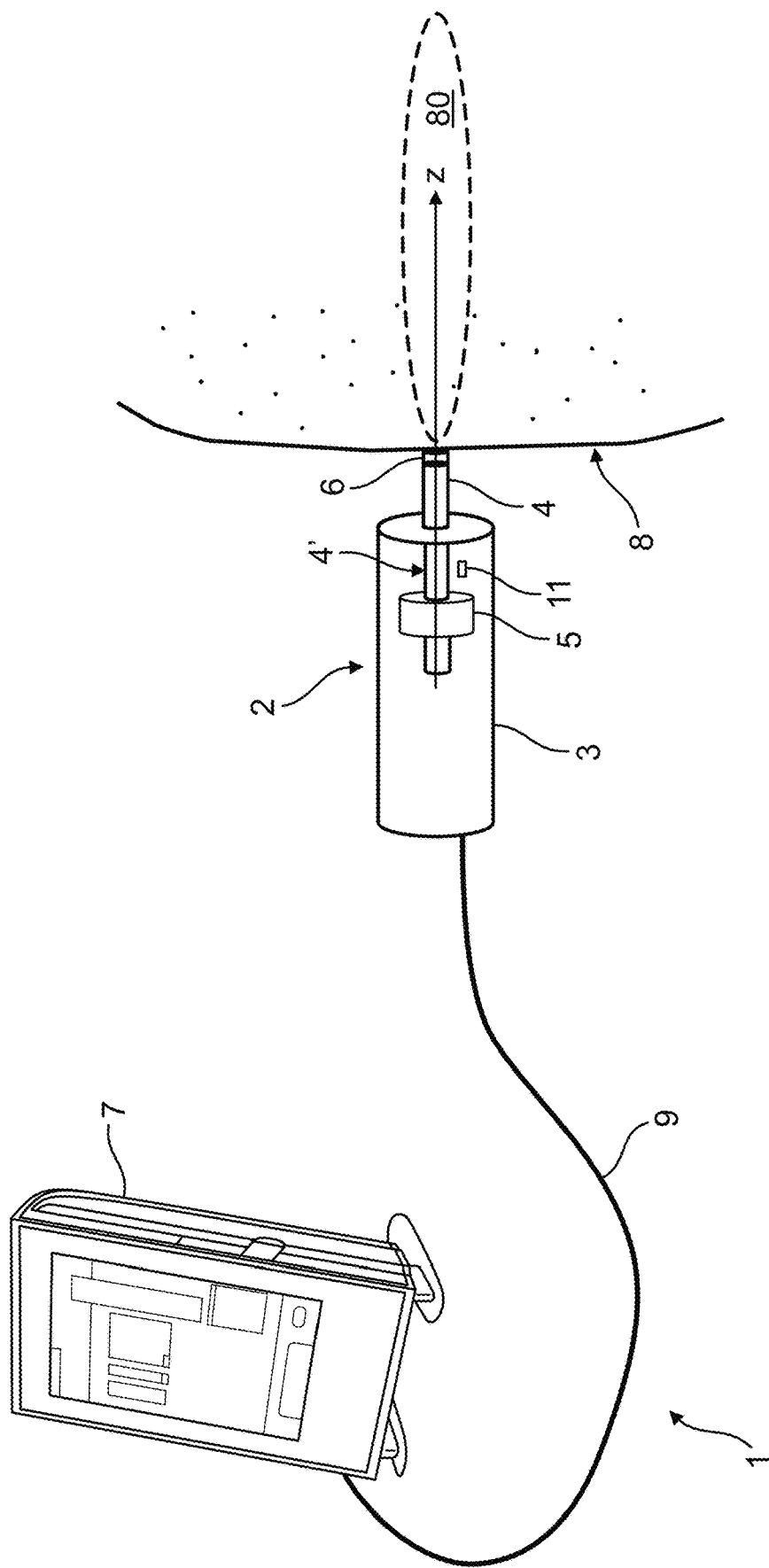
FIG. 6 schematically represents an elastography device according to the instant technology.

FIG. 6 represents an exemplary embodiment of such an elastography device 1. This elastography device 1 comprises a probe 2 including a probe casing 3 (which forms the main body of the probe), to be handheld, and a protruding part, which protrudes from the casing 3. The protruding part can thus be applied against the body 8 of the subject, to deliver mechanical pulses to it, and to transmit and acquire U/S shots. In this embodiment, the protruding part is a tip 4, for instance a cylindrical tip (with a circular transducer 6 at its end).

Still, in other embodiments, the protruding part could be an ultrasound head (located at an end of the probe) including an array, for instance a linear array of U/S transducers. In this regard, it may be noted that the proposed technique can be used with a single element ultrasound transducer (like in the case of FIG. 6), or with a multi-element ultrasound transducer (like an array of U/S transducers). While a single element ultrasound transducer is adapted to display A-mode and M-mode ultrasound imaging, a multi element ultrasound transducer can also display a B-mode image allowing an easier localization of the to-be-measured tissue. In the case of a multi element ultrasound transducer, at least one of the beamformed ultrasound lines is used to track how the probing and measurement pulses propagate. To this end, using the center beamformed ultrasound line (which is aligned with the probe axis) is beneficial, for symmetry considerations.

The probe 2 comprises also a low frequency vibrator 5, and the U/S transducer 6, which is fixed at an end of a tip 4. Here, the U/S transducer 6, plays both the role of an ultrasound emitter and the role of an ultrasound receiver (alternatively). Still, in other embodiments, the probe may comprise an U/S emitter and an U/S receiver distinct from each other. Here, the U/S transducer 6 is arranged on the axis z of the vibrator. Still, in other embodiments, the U/S transducer could be arranged elsewhere on the probe, not necessarily on the vibrator's axis.

The tip 4 is actuated by the low frequency vibrator 5. Here, the vibrator 5 is arranged to move the tip 4 relative to the probe casing 3. The vibrator 5 is arranged to move a shaft 4', the end of which forming the tip 4 of the probe. Still, in other embodiments, the tip, or, more generally, the protruding part of the probe, could be bound to the probe casing with no motion with respect to the probe casing, the vibrator being then arranged to move a mass, inside the casing, to make the whole probe moving towards the tissue and back (by virtue of a recoil effect).

The vibrator 5 is a low frequency vibrator in that it moves the tip with a central, average frequency smaller than 500 hertz, or even smaller than 100 hertz (in contrast with ultrasound shots or echo signals, whose central frequency is typically higher than 1 megahertz, for instance between 1 and 5 megahertz). The vibrator is a low-frequency electromechanical actuator, for instance with one or several coils and magnets, similar to a loud-speaker actuator.

In this device 1, the vibrator 5 is rotationally symmetrical around a vibrator axis, which coincide with the probe axis z. When the vibrator 5 vibrates, it induces displacements that are mainly longitudinal, parallel to its axis. The shaft 4' is centered onto the axis z, and the vibrator 5 is arranged to move this shaft along the axis z.

In practice, the displacement of the ultrasound transducer 6, induced by the vibrator 5, has a peak-to-peak amplitude between 0.1 mm and 10 mm (for instance between 1 and 4 or between 1 and 5 mm for the transient elastography measurement in itself, and possibly smaller for a probing pulses, employed to guide the operator).

The probe 2 comprises a displacement sensor 11, arranged to output a measurement signal $S_d$ representative of the displacement of the ultrasound transducer 6. In this embodiment, the measurement signal $S_d$ is representative of the displacement of the ultrasound transducer 6 relative to the probe casing 3. A part of the displacement sensor 11 is fixed on the shaft mentioned above while another part of the sensor is fitted in the probe, with no motion with respect to the casing 3. The displacement sensor 11 may be a Hall-effect sensor, an induction displacement sensor, or any other suitable sensor.

Figure 7:
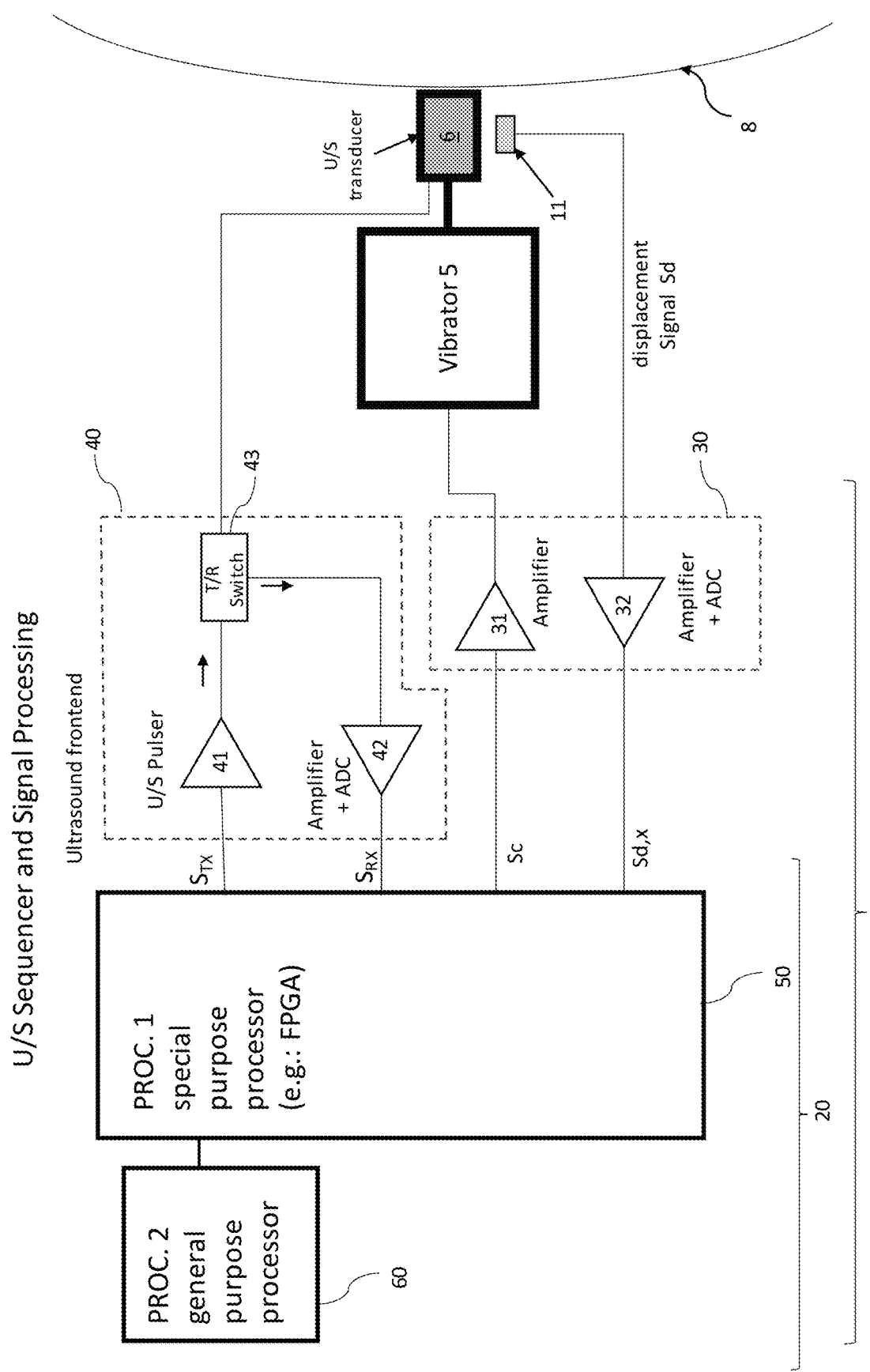
FIG. 7 schematically represents some elements of an electronic unit of the device of FIG. 6.

The device 1 comprises also an electronic unit 10, connected to the vibrator 5 and to the U/S transducer 6. A block diagram of a possible embodiment of the electronic unit 10 is represented in FIG. 7. The electronic unit 10 of FIG. 7 comprises a control and processing module 20, an ultrasound front end 40, and a motion controller 30 to control the vibrator 5.

The ultrasound front end 40 and the motion controller 30 are both connected to the control and processing module 20 (that is to say that they can receive instructions or control signals from the control and processing module 20 or send data or measurement signals to it). The electronic unit comprises also a signal conditioning module 32, to condition and digitalize the measurement signal Sd outputted by the displacement sensor 11. This signal conditioning module 32 is part of the motion controller 30, here.

The motion controller 30 comprises also an amplifier 31, to drive the vibrator 5. The amplifier 31 is configured to convert a control signal Sc into a form suitable to drive the vibrator, from an electrical point of view. The amplifier 31 may thus be a current amplifier or a power amplifier (such as the LM3886 power amplifier by texas instrument, for instance), for instance.

The ultrasound front end 40 comprises an ultrasound (U/S) pulser 41, an U/S receiver module 42 and a switch 43 for alternatively transmitting and receiving ultrasonic signals. The U/S pulser 41 comprises an electric circuit configured to generate an electric ultrasonic signal appropriate to drive the U/S transducer 6, based on a transmission control signal $S_{TX}$ outputted by the control and processing module 20. The U/S receiver module 42 comprises an electric circuit configured to acquire an electric ultrasonic signal (an echo signal), previously received by the U/S transducer 6 (and transmitted to the U/S receiver module 42 via the switch 43), and to transmit the corresponding (digitalized) U/S reception signal $S_{R,X}$ to the control and processing module 20. The electric circuit of the ultrasonic receiver module 42 may comprise a voltage amplifier, one or more filters and an analog to digital converter (ADC), for instance an 8 to 16 bits ADC with a 10 to 100 Mega-sample per second rate.

The control and processing module 20 is a device or system comprising electric circuitry for processing data, such as a microprocessor coupled to a non-volatile non-transitory memory comprising machine executable instructions and/or a programmable microcircuit like an FPGA or another programmable circuit. The control and processing module 20 may also comprise one or several Random Access Memories or RAMS memories or registers. Anyhow, the control and processing module 20 comprises at least one, here two processors 50, 60 and at least one memory.

Figure 8:
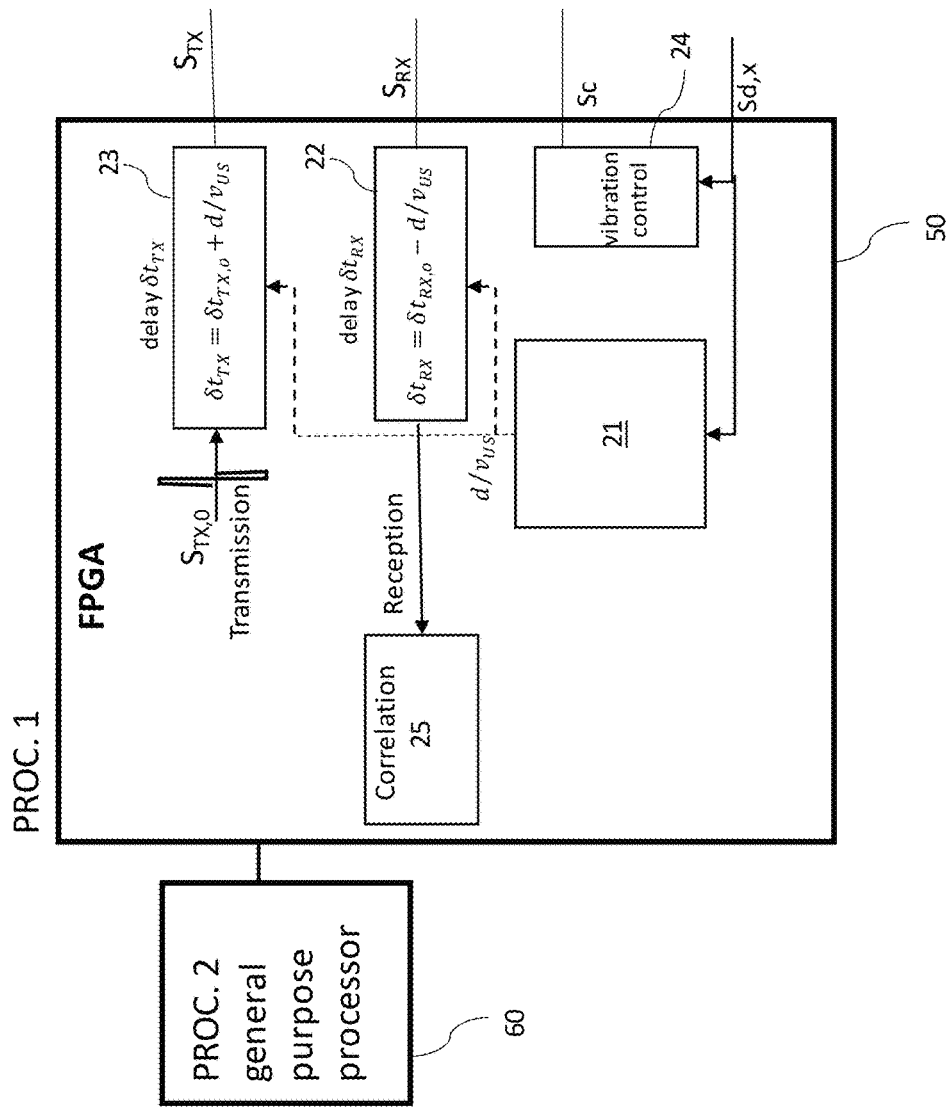
FIG. 8 schematically represents in more detail a control and processing module 20 of this electronic unit.

Some sub-modules of the control and processing module 20, that are implementing a technique of pre-compensation of the transducer's displacement, are represented in more details in FIG. 8. They will be presented later.

Some of the elements of this electronic unit 10 (such as the signal conditioning module 32, for instance) can be housed in the probe 2 while other elements of this unit 10 (like the general-purpose processor 60) may be remote. Alternatively, the entire electronic unit could be housed in the probe 2, or, on the contrary, it could be entirely located outside the probe.

The probe 2 is operatively connected to a central unit 7, which has the structure of a computer (and that could be a laptop, a smartphone, or a dedicated electronic device arranged to control and to interface the probe, and to process the signals acquired). The central unit comprises at least a memory and a processor. Here, it comprises also a user interface, such as a touch screen. The probe may be connected to the central unit 7 by a connection cable 9, or by a wireless link. Here, some elements of the electronic unit 10 (in particular the general-purpose processor 60) are part of the central unit 7.

The electronic unit 10 (more specifically, its control and processing module 20, here) is configured (for instance, programmed via instruction stored in a memory) to control the electronic device 1 so that it operates alternatively (a) in a guidance mode to determine whether the probe 2 is correctly positioned in front of a region 80 of the body 8 to be probed to carry out a measurement of a mechanical property of the probed region 80 and (b) in a measurement mode to carry out the measurement.

When the elastography device 1 is operated in the guidance mode (phase S1, in FIG. 9), the electronic unit 10 controls the low frequency vibrator 5 to deliver to the body 8 of the subject, successively and repeatedly, a plurality of probing pulses PRB, each probing pulse being a transient, low frequency mechanical pulse. As mentioned above, delivering (and tracking) these probing pulses enable to test an aptitude of the region 80, located in front region of the probe, to transmit transient pulses, and enables to test a homogeneity of this region with respect to the propagation of such transient pulses. It enables in particular to determine a propagation quality indicator Q, representative of the aptitude of this region to transmit the probing pulses and of its homogeneity with respect to this propagation. This allows the operator to know if the probe is located in front of, and directed towards a homogeneous organ of sufficiently large dimensions, and therefore if it is suitably positioned for a measurement by Vibration-Controlled-Transient-Elastography.

The operation of the elastography device in the guidance mode will be presented first. And the measurement mode will then be presented.

In the guidance mode (phase S1, in FIG. 9), as already mentioned, the electronic unit 10 controls the low frequency vibrator 5 to deliver to the body 8 of the subject, successively and repeatedly, a plurality of probing pulses PRB, each probing pulse being a transient, low frequency mechanical pulse.

The guidance mode may be triggered in response to a manual triggering by the operator, achieved for instance by means of the touch screen of the central unit 7.

In the embodiment described here, once in the guidance mode, when the electronic unit 10 detects that the tip 4 is applied against the body 8 of the subject, the electronic unit 10 controls the vibrator so that the probing pulses are continuously, automatically repeated (i.e.: without needing a manual triggering again), as long as the tip remains in contact with the body of the subject 8. The electronic unit 10 may detect that the tip 4 is applied against the body 8 of the subject based on a contact force level F1 (measured by a force sensor—not represented on the figures—like a strain gauge, or deduced from the position of the shaft 4', pushed into the casing when the tip is pressed on the subject's body). Conditioning the generation of the probing pulses upon such a contact detection is beneficial as it prevents from having the probe vibrating when no probing would actually be possible (and when it is only supported by the hand of the operator).

Anyhow, should the generation of the probing pulses be conditioned or not upon such a contact detection, when in the guidance mode, the probing pulses are continuously, automatically repeated (i.e.: without needing a manual triggering).

The electronic unit 10 controls the vibrator 5 so that it delivers the probing pulses, using the motion controller 30. More specifically, the shaft 4' displacement d is controlled according to a predetermined command signal. Here, this displacement is controlled by a control-loop comprising the amplifier 31, the displacement sensor 11, the signal conditioning module 32, and a vibration control module 24 (FIG. 8), such as a PID (proportional, integral, derivative) corrector (still, in alternative embodiments, the vibrator may be controlled by an open loop—that is with no sensor feedback).

In the guidance mode, the probing pulses are delivered with a rate of several pulses per second, for instance a rate of 5 or even 10 pulses per second or more. So, the probing pulses PRB are repeated with a repetition period $T_G$ which is quite short, typically below 0.2, or even 0.1 second. Delivering the probing pulses with such a rate is beneficial, because it allows for an almost continuous guidance, for the operator. It also allows for averaging the results corresponding to a few successive probing pulses and transmitting corresponding (averaged) guidance information with a low lag time. Besides, thanks to this quite high repetition rate, the probing results thus averaged are obtained in a rather short time, compared to the typical time with which organ moves, in the body of the subject (due to respiratory motion or cardiac pulses).

Each probing pulse PRB has a duration $T_1$ (which is the time during which there is a substantial motion protruding part—induced by the vibrator), followed by a downtime during which there is no or substantially no motion of the protruding part, before another probing pulse PRB is generated. An actuation ratio (in other words, a duty cycle), equal to the pulse's duration $T_1$, divided by the period $T_G$ with which the probing pulses are repeated, is thus smaller than 1, for instance below 50%, or even below 20%.

Each probing pulse has a limited amplitude, smaller than that of the measurement pulses (identified as reference character "MSR" in FIG. 9) delivered in the measurement mode. This reduced amplitude makes the guidance comfortable for the subject under examination, among over benefits. For example, each probing pulse may correspond to a 1 mm peak-to-peak displacement $A_1$ of the tip 4, this displacement being two times smaller than the peak-to-peak displacement $A_2$ of the tip for each of the measurement pulse MSR.

Regarding the central frequency of each probing pulse PRB, it is slightly reduced, compared to that of the measurement pulses MSR, to improve the comfort of the subject receiving the probing pulses and to increase the depth of penetration within the medium, as explained in detail in the section entitled "summary". Here, the elastography device is a device suitable for characterizing liver. The central frequency $f_{c,1}$ of each probing pulse PRB is comprises between 20 Hz and 45 Hz, and its duration $T_1$ may, like here, be below $5/f_{c,1}$, or even below $3/f_{c,1}$.

Each probing pulse may consist of one period, or a few periods (typically less than 2 or 3 periods) of a sinusoid whose frequency (which is equal, or close to the central frequency mentioned above) is comprised between 20 Hz and 45 Hz.

Figure 9:
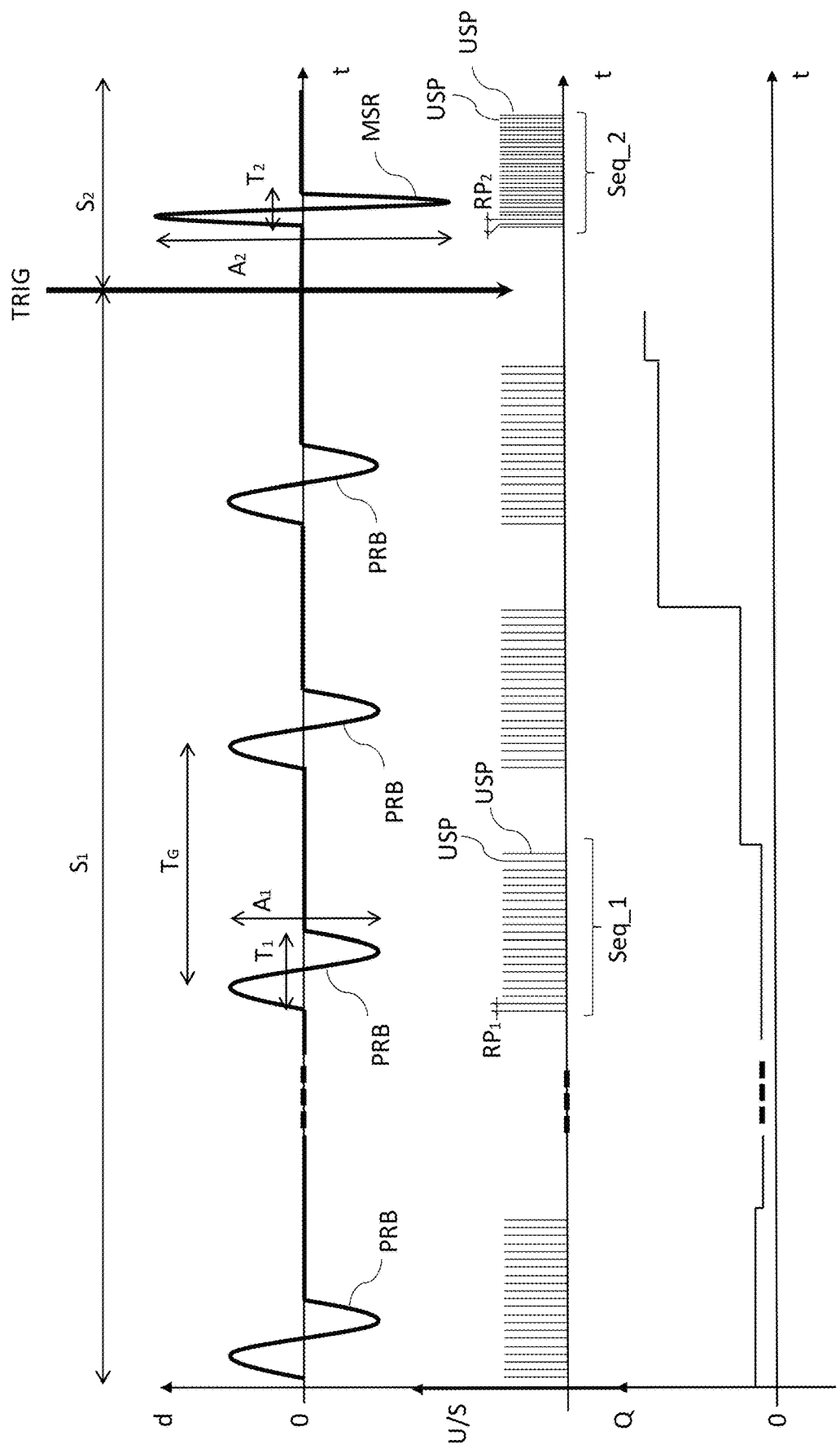
FIG. 9 schematically represents a sequence of mechanical and ultrasound pulses emitted by the device of FIG. 6.

In the example of FIG. 9, for instance, each probing pulse consists in one period of a sinusoid at 40 Hz, and the value of its duration $T_1$ is thus 25 ms. In this example, each probing pulse is followed by a downtime of 75 ms (and so $T_G$=0.1 s); the probing pulses are repeated with a rate of 10 pulses per second (and, as will be described below, the propagation quality indicator Q is computed by means of a rolling average, averaging the results corresponding to 3 to 5 successive probing pulses). Alternatively, the downtime could be 25 ms, for example (with $T_G$=0.05 s), the probing pulses being then repeated with a rate of 20 pulses per second.

For each probing pulse PRB, the electronic unit 10 controls the ultrasound transducer 6 (by means of the U/S pulser 41 of the U/S front end 40, among others) so that the U/S transducer 6 emits a sequence of ultrasound pulses Seq_1, and acquires echo signals received in response by the ultrasound transducer 6, to track how the probing pulse PRB propagates through the probed region 80 of the body 8 of the subject, located in front of the tip 4 of the probe.

For this sequence Seq_1, and for the sequence of ultrasound pulses Seq_2 emitted in the measurement mode (to track how the measurement pulse MSR propagates), the central frequency of each ultrasound pulse USP is comprised for instance between 0.5 and 10 megahertz. The ultrasound pulses of the sequence Seq_1, or Seq_2 may be transmitted one at a time, two successive pulses being separated by a pulse repetition period $RP_1$, $RP_2$, this pulse repetition period being typically between 100 microseconds and 2 milliseconds (which corresponds to a pulse repetition rate between 0.5 kilohertz and 10 kilohertz). The ultrasound pulses of the sequence mentioned above may also be transmitted by groups, for instance by groups of two pulses (to compute correlations between the two corresponding echo signals). The two pulses of each group may be separated by duration between 50 and 200 microseconds, while the groups of pulses themselves are separated by a longer duration, for instance higher than 0.2 or 0.5 ms. It will be appreciated that other transmission sequences can also be considered in various embodiments. Regarding the total duration of the sequence of U/S pulses Seq_1, Seq_2, it may be between 25 ms and 200 ms. This duration may be selected depending on the speed of propagation of the elastic wave which is the slower and depending on the depth of the region to be observed. For instance, for an 80 mm depth and a speed of propagation of the 1 m/s (typical for shear waves in the liver of a subject), the sequence may have a duration of 80 ms.

Regarding the echo signals, acquired to track the propagation of the mechanical pulse considered, each of them is formed by a signal, received over time t by the U/S transducer 6 after the emission of one of the U/S pulses USP. It is more precisely the signal received within a given temporal window starting after this emission and having a given duration.

In the embodiment described here, in the guidance mode, the U/S pulses repetition rate (that is, $1/RP_1$) is lower than the repetition rate of the U/S pulses in the measurement mode (that is, $1/RP_2$), for instance, at least 20% lower, and possibly at least two times lower. For example, in sequence Seq_1 (in the guidance mode) the U/S pulse repetition rate may be between 0.5 and 3 kHz (e.g.: 2 kHz), while in sequence Seq_2 (in the measurement mode), the U/S pulse repetition rate may be between 2 and 10 kHz (e.g.: 6 kHz). As explained in detail in the section "summary", employing a lower U/S pulse repetition rate in the guidance mode is beneficial in terms of acoustic output power emitted by the elastography device, and in terms of computation time. And it is well adapted to the probing pulses PRB, whose central frequency and amplitude $A_1$ are lower than the central frequency and amplitude $A_2$ of the measurement pulse MSR.

In the guidance mode, for each probing pulse PRB, the electronic unit 10 determines the propagation quality indicator Q mentioned above. This indicator is determined from the echo signals acquired to track how this probing pulse PRB travels in the probed region 80.

As mentioned above, the propagation quality indicator Q is representative of an aptitude of the probed region 80 to transmit the probing pulse PRB, that is to say to let the probing pulse propagate through it, to penetrate in depth to this region (for instance over a given depth at least), even if the probing pulse may be damped, and possibly, partially distorted during this propagation. The propagation quality indicator Q is also representative of the homogeneity of the probed region 80 with respect to the propagation of the probing pulse PRB; in other words, it is representative of an absence of substantial propagation inhomogeneity, such as rebounds, discontinuities, or changes/steps in the speed of propagation of the probing pulse.

The propagation quality indicator Q may specify whether spatio-temporal characteristics of tissue strain (that is to say characteristics representative of the variation of the tissue strain, both as a function of time and as a function of at least one spatial coordinate), caused by the probing pulse delivered to the body of the subject, correspond to the propagation of a low frequency mechanical transient pulse, in a homogeneous medium.

Figure 1:
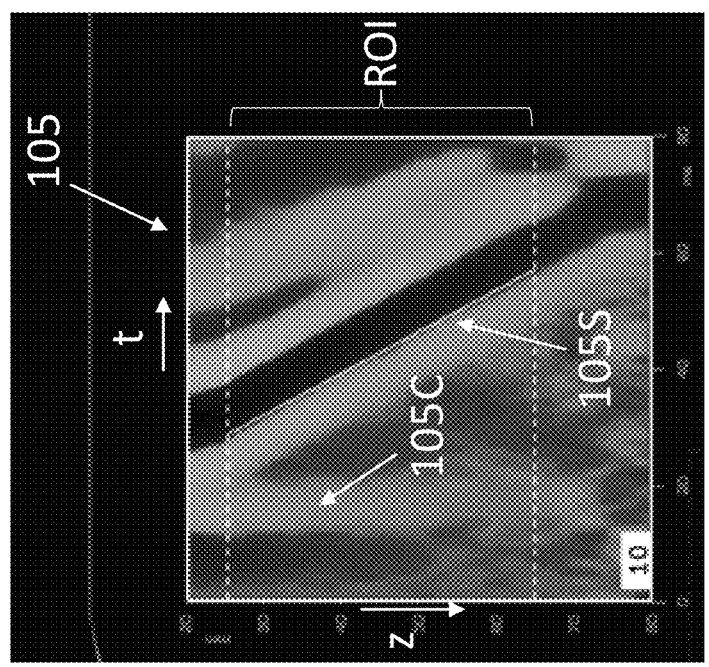
FIG. 1 shows an exemplary elastogram.
Figure 10:
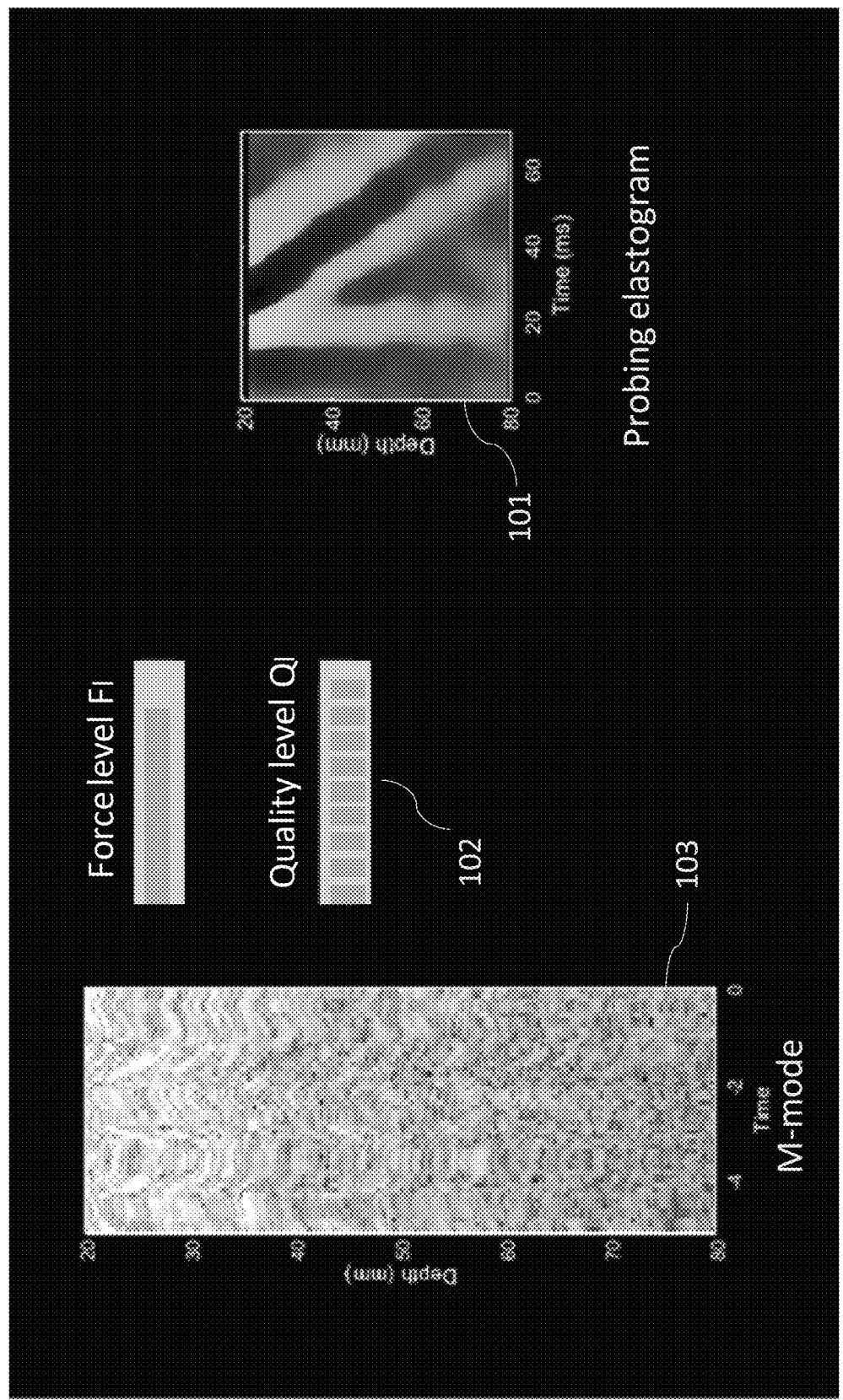
FIGS. 10 and 11 schematically represents information displayed by the device of FIG. 6, respectively when operating in a guidance mode, and when operating in a measurement m ode.
Figure 11:
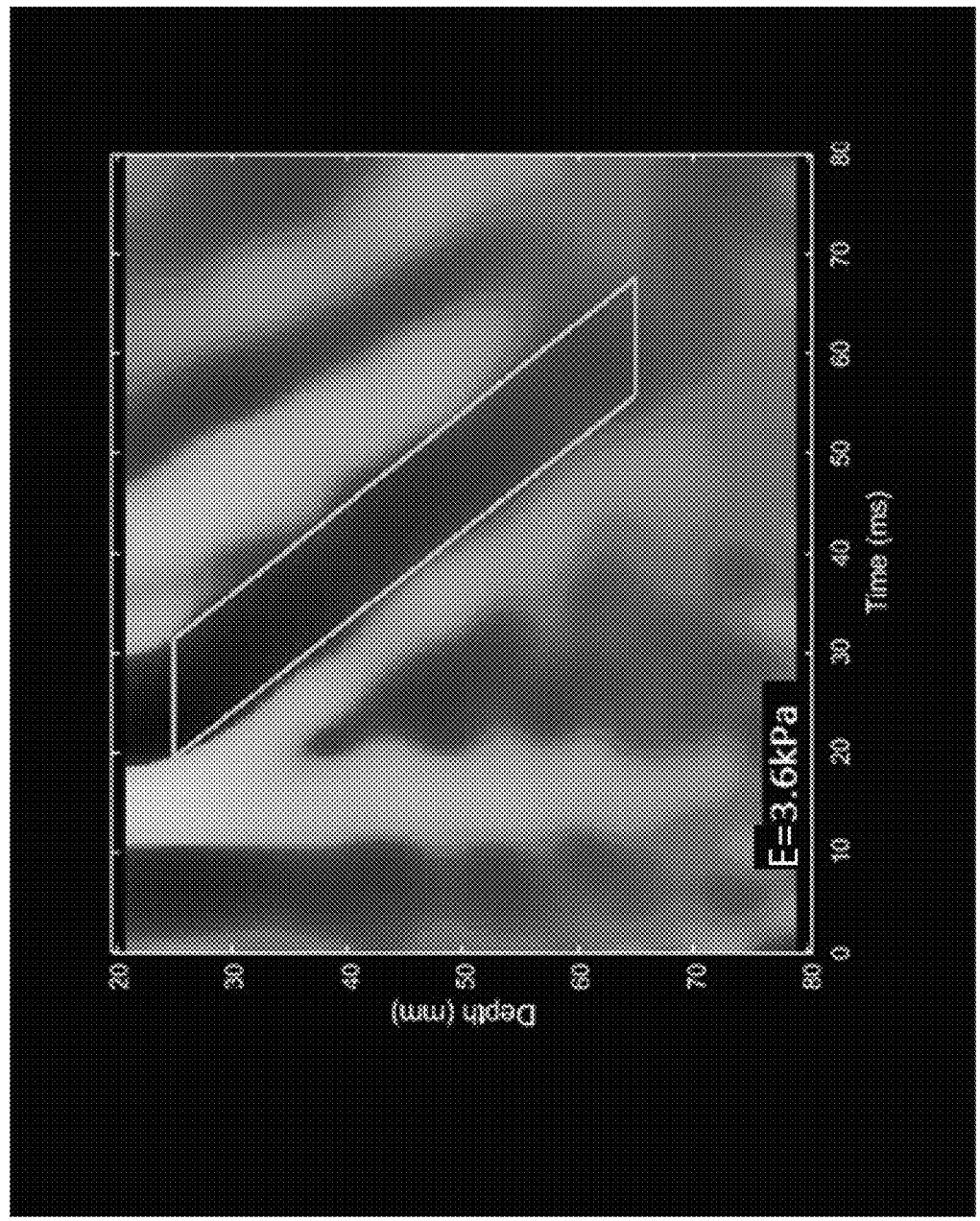

In the embodiment described here, in the guidance mode, for each probing pulse PRB, the electronic unit determines tissue strain data, representative of tissue strain within the probed region 80, as a function of time t and as a function of depth z within the probed region 80. The tissue strain data is determined from the echo signals acquired to track how the probing pulse PRB propagates through the probed region. As mentioned above, when represented graphically, as a function of time and depth (like in FIG. 1, 10, or 11), such tissue strain data forms an elastogram.

The tissue strain data is determined, from the echo signals, using a correlation technique or another patterning matching algorithm, to determine how portions of the tissue move under the influence of the elastic wave that is passing through it (the elastic wave being generated by the periodic mechanical vibration delivered by the system). For instance, for each couple of two successively received echo signals, the two echo signals are correlated with each other, by means of the correlation module 25 (FIG. 8), which enables to determine tissue displacement (namely, the tissue displacement that occurred between the two U/S pulses), as a function of depth, and at given time. The electronic unit then determines the propagation quality indicator Q based on the tissue stain data corresponding to this probing pulse.

The propagation quality indicator Q may be determined so as to specify whether an elastogram, representing the tissue strain data, comprises one, or a few, regular stripes (in the t-z coordinates plane).

It may also be determined, like here, to specify whether a probing pulse time of flight varies linearly and smoothly and with depth z, or not. To this end, the propagation quality indicator Q could be derived from a coefficient of determination $R^2$ of a linear regression applied to the probing pulse time of flight, as a function of depth. The propagation quality indicator Q may even correspond directly to this coefficient of determination. The probing pulse time of flight in question is the time taken by the probing pulse to propagate, from the surface of the body 8 of the subject, to a given depth within the probed region 80 (in other words, to reach the depth considered). This time of flight may be determined by computing a Fourier transform the tissue strain at the depth considered (tissue strain as a function of time, at a fixed depth), and then deriving the time of flight from the phase of a component of this Fourier Transform (typically, the component whose frequency is the central frequency of the probing pulse delivered by the probe). It may also be determined using other techniques, for instance a zero-crossing technique or a pattern matching technique. When a zero-crossing technique is employed, the time of flight may be determined as a time at which the tissue strain crosses zero, for the depth considered (crosses zero and then remains on the same side of the zero-line for some time, to avoid noise-induced non-relevant crossings). When a pattern matching technique is employed, the time of flight may be determined as a time-offset that enables to best match a given (reference) pulse profile with the variation of tissue strain with time, at the depth considered.

In the embodiment described here, the propagation quality indicator Q is a numerical value (for instance comprises between 0 and 1). Still, in other embodiments, the propagation quality indicator Q could directly take the form of the elastogram representing the tissue strain data. Indeed, such an elastogram enables the operator, just as the numerical value mentioned above, to readily determine whether the tissue is homogeneous and suitable for elastic wave propagation or not.

In the guidance mode, for each probing pulse PRB, the electronic unit 10 controls the elastography device 1 to transmit guidance information, the guidance information being based on the propagation quality indicator Q. In practice, the guidance information is transmitted, communicated to the operator of the device 1 (visually and/or using audible signals).

The guidance information could comprise the elastogram representing the tissue strain data. It may also comprise of the propagation quality indicator Q itself (i.e.: as it is, with no further processing). The guidance information may take the form of a binary (for instance red/green) indicator, whose value specifies whether the propagation quality indicator Q is above or below a given quality threshold. The guidance information may also be a composite element gathering the different features mentioned above (and, possibly, other features), these features remaining distinct from each other (i.e.: unfused), in the guidance information. It is the case here, where the guidance information, provided to the operator, comprises:

- an elastogram 101 (which a probing, or guiding elastogram), which is an averaged elastogram, as will be explained below,
- a display 102 of a quality level QI, in the form of a pointer indicator, or bar-scale indicator or equivalent; the quality level QI may be the propagation quality indicator Q itself, or, like here, a level combining (merging), in the form of a single level, the propagation quality indicator Q and an ultrasound-based guiding information (for instance by computing the mean of these two quantities), and
- a binary (green/red) indicator, determined by comparing the quality level QI with a preset threshold; this binary indicator is displayed by switching on, or on the contrary, off, a LED arranged on the probe casing 3.

The elastogram 101 and the quality level QI are displayed on the screen of the central unit 7. The force level F1 and an ultrasound echoes M-mode display 103 are also displayed on this screen, as they are useful to help the operator adequately positioning the probe. The ultrasound echoes M-mode display 103 a 2-dimensional image in which each column represents one of the ultrasound echo signals acquired, the U/S echo signals successively acquired being displayed one aside the other.

As mentioned above, the quality level QI combines the propagation quality indicator Q and the ultrasound-based guiding information mentioned above. As explained in the section "summary", the ultrasound-based guiding information may be determined from the ultrasound echo signals, so as to be representative of the more or less homogeneous nature of the region located in front of the probe with respect to U/S propagation and/or to be representative of the fact that the U/S attenuation in this region is within an attenuation range expected for the organ to be characterized. It is important to note that ultrasound-based guiding information cannot predict the propagation of shear waves with a good accuracy as ultrasound signals are not sensitive enough to the mechanical properties of soft tissues.

As mentioned above, the electronic unit 10 determines the propagation quality indicator Q for each probing pulse PRB, in the guidance mode. For each new probing pulse PRB delivered to the body of the subject, the corresponding propagation results (e.g.: the tissue strain data) are taken into account determine a new value of the propagation quality indicator Q.

This new value of the propagation quality indicator Q can be determined based on the propagation results of this new probing pulse only.

This new value may also be determined based on the propagation results of associated to more than one probing pulse, for instance by averaging these different propagation results and then computing the propagation quality indicator Q. In this case, the propagation quality indicator Q may be updated after each probing pulse (by using a rolling average, for instance), which enables a real-time (or an almost real-time) monitoring, for the operator. Alternatively, the propagation quality indicator Q could be updated only after a few new probing pulses are delivered (in which case a classical, non-rolling average can be employed).

In the embodiment described here, the propagation quality indicator Q is determined based on the propagation results corresponding respectively to several probing pulses, typically between 3 and 6 successive pulses (e.g.: 5), these different propagation results being averaged, by rolling averaging. For each new probing pulse, the corresponding elastogram (or, in other words, the corresponding tissue strain data) is determined (by correlation), and is then averaged with the elastograms corresponding respectively to the four preceding probing pulses, to obtain an averaged elastogram 101, which is then displayed. A new value of the propagation quality indicator Q is then computed, from this averaged elastogram (averaged tissue strain data).

This averaging, of the results corresponding respectively to a few quickly-repeated probing pulses, is beneficial as it increases the signal-to-noise ratio of the averaged probing elastogram (see FIG. 12, inserts a) and a')), while allowing for an almost continuous monitoring of the more or less adequate positioning of the probe 2.

Figure 12:
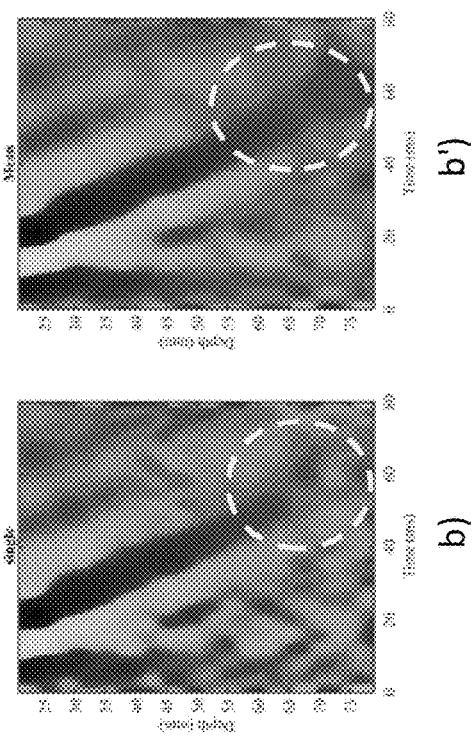
FIG. 12 shows different elastograms obtained, respectively, without and with an averaging over several successive probing pulses.
Figure 12:
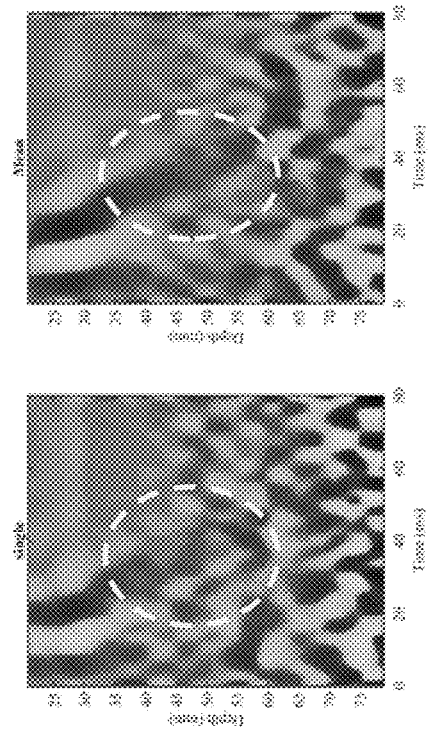
Figure 12:
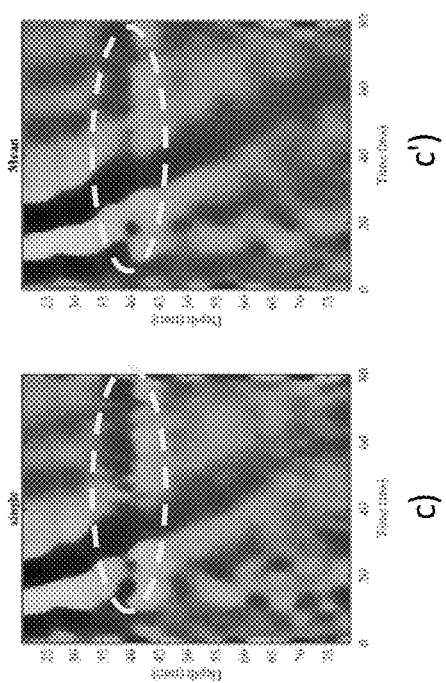

FIG. 12 shows different elastograms measured in vivo (when pointing at the liver of a subject), with, and without averaging. The averaged elastograms are obtained by averaging 5 successive elastograms acquired at a rate of 10 elastograms per second. Elastogram a) is one of the 5 elastograms averaged together to obtain the averaged elastogram a'). This example illustrates the signal-to-noise ratio improvement due to this averaging technique (in particular in the part of the graph surrounded by the dashed-line). Elastogram b) and c) are also single, non-averaged elastograms corresponding to the averaged elastograms b') and c'). Elastograms b) and b') illustrate that this averaging technique also increases the depth until which a probing pulse can be tracked and visualized. And elastograms c) and c') illustrate that it also reduces the influence of possible artefacts, caused for instance by the presence of a blood vessel or another inhomogeneity in the region of interest.

The operation of the elastography device 1 in the measurement mode (phase S2, in FIG. 9 is now described in more detail.

The elastography device 1 may be configured to switch from an operation in the guidance mode, to an operation in the measurement mode (phase S2, in FIG. 9) in response to a manual triggering by the operator. This manual triggering may be achieved by actuating a push-button switch arranged on the probe casing 3, or by actuating a foot-switch, for instance. In such a case, when the operator considers, based on the guidance information, that the position and direction of the probe 2 is adequate, he triggers the measurement mode, so that a measurement of at least one mechanical property of the probed region, related to low frequency elastic wave propagation (for instance its young modulus) is measured.

The elastography device may also be configured to switch from the guidance mode to the measurement mode automatically, when a given criteria is fulfilled. For instance, this switching may occur when the propagation quality indicator Q (or the quality level mentioned above) becomes past (e.g. higher than) a given quality threshold. Other criteria, that take into account other parameters, in addition to or alternatively to the propagation quality indicator Q may also be employed, to make the elastography device automatically switch from the guidance mode to the measurement mode. The automatic switching described herein may be implemented using one or more electronic circuits including, for example, a comparator.

Once in the measurement mode, the electronic unit 10 controls the low frequency vibrator 5 to deliver to the probed region at least one, here a plurality of successive measurement pulses MSR, each measurement pulse being a transient low frequency mechanical pulse. The electronic unit 10 also controls the U/S transducer 6 to emit a sequence Seq_2 of ultrasound pulses USP, and acquires echo signals received in response to track how each measurement pulse MSR propagates through the probed region 80.

For each measurement pulse, the electronic unit 10 processes the echo signals acquired, to determine tissue strain data representative of tissue strain within the probed region, as a function of depth z and time t, as explained above about the probing pulses.

The electronic unit 10 then determines the mechanical property of the probed region 80, from the tissue strain data.

Here, the electronic unit 10 determines this mechanical property by averaging, taking into account the tissue strain data associated respectively to the different measurement pulses delivered to the body of the subject. In practice, the number of measurement pulses MSR, delivered due to the switching in the measurement mode, may be between 2 and 10, for instance, and they may be delivered with a rate between 3 and 20 pulses per second. The tissue strain data associated respectively to these different measurement pulses, are averaged together, to obtain an averaged tissue strain data, and a corresponding averaged measurement elastogram, such as the one represented in FIG. 11. The mechanical property of the probed region is then determined from this averaged tissue strain data. The number of successive measurement pulses MSR taken into account in this averaged tissue strain data may be the same as the number of successive probing pulses PRB averaged together to produce the average guiding elastogram 101, in the guidance mode (and the corresponding repetition rates could also be the same).

The mechanical property of the tissue, related to low frequency shear wave propagation may be a quantity related to the tissue stiffness, such as the propagation speed of shear waves $V_s$, the shear modulus of the tissue or the Young's modulus E of the tissue (which can be derived from the slope of the stripes identified in the elastogram, or from the variation of the time of flight of the measurement pulse as a function of depth). It may also be a quantity related to low frequency shear wave attenuation in the tissue, like viscosity.

As mentioned, when describing the operation in the guidance mode, each measurement pulse MSR has an amplitude $A_2$ higher than the amplitude $A_1$ of each of the probing pulses PRB. The peak-to-peak amplitude $A_2$ of the displacement of the tip 4 of the probe may for instance be between 1 and 4 mm, for the measurement pulse. Besides, the central frequency of each measurement pulse MSR may, like here, be higher than that of any of the probing pulse PRB. The central frequency of each measurement pulse MSR may be between 50 and 200 Hz, for instance, when the elastography device is, like here, configured to characterize the liver of patients. Here, each measurement pulse comprises of one period of a sinusoid whose frequency is between 50 and 200 Hz, here equal to 50 Hz. Each measurement pulse is followed by a downtime, whose duration is higher than a duration $T_2$ of the measurement pulse (and possibly higher than two or three times this duration). As already mentioned, the ultrasound pulses repetition rate is higher, in sequence Seq_2, than in the U/S sequence Seq_1 emitted to track one of the probing pulses. In sequence Seq_2, the U/S pulses repetition rate may be between 2 and 10 kHz for instance. Here, it is equal to 6 kHz for example.

According to an optional feature, the electronic unit 10 may be configured to adjust the central frequency of the measurement pulses, based on a property of the probed region 80 previously determined in the guidance mode, using at least one of the probing pulses (this property being determined based on how the probing pulse propagates through the probed region). More generally, the characteristics of the measurement pulse or pulses (in terms of frequency and amplitude) may be adjusted based on the preliminary characterization of the probed region 80 achieved thanks to the probing pulses.

This property may be representative of an attenuation underwent by the probing pulse during its propagation within said region for instance. In this case, the electronic unit may be configured to adjust the central frequency of the measurement pulse or pulses so that it is all the higher as the attenuation in the region is high (which enables to obtain a desired depth of penetration, for the measurement pulse, even if the elastic waves attenuation is high in the probed region—higher than expected, in average, for liver, for instance).

The optional pre-compensation technique mentioned above (with reference to FIG. 7) is presented now, with reference to FIG. 8.

When processing the ultrasound echo signals acquired, in order to determine tissue strain, it is desirable to compensate for the tip's displacement d. Indeed, as the ultrasound pulses sent to probe the medium displacement are emitted by the tip end, the tip displacement, which is quite significant, adds up to the to-be measured tissue displacement. To reduce the correlation computation time, and to increase the signal-to-noise ratio, it is thus desirable to compensate for this displacement. Known compensation techniques are based on a post-processing of the echo signals, in which strong echoes are identified and employed to realign temporally these signals. But such a technique is time-consuming, and not well suited to be implemented in a special purpose processor like processor 60 (which may be an FPGA, for instance). So, in order to compensate for this displacement d, the electronic unit 10 (more specifically, its processor 60) is configured here to implement the following pre-compensation technique.

The ultrasound pulses emitted to track the probing and measurement pulses are emitted with:
 a temporal offset upon emission $\delta t_{TX}$, by which the emission of an ultrasound pulse is shifted,
 and/or a temporal offset upon reception $\delta t_{RX}$, by which an echo signal, acquired in response to said emitted ultrasound pulse, is shifted, so as to compensate for a temporal shift of said echo signal with respect to other echo signals acquired, caused by the displacement d of the ultrasound transducer 6 (or plurality of ultrasound transducers),
 the temporal offset upon emission $\delta t_{TX}$ and/or the temporal offset upon reception $\delta t_{RX}$ being adjusted so that a difference thereof is equal to $\Delta t_0 - 2 \cdot d / v_{us}$, $\Delta t_0$ being a constant delay and $v_{us}$ being the speed of ultrasound in the tissue under examination.

The transducer's displacement is thus compensated from the beginning, without requiring a special post-processing.

In the case of FIG. 8, the elastography device is more specifically configured so that the temporal offset upon emission is equal to $\delta t_{TX,0} + d/v_{us}$, $\delta t_{TX,0}$ being a constant delay upon emission, while the temporal offset upon reception is equal to $\delta t_{RX,0} - d/v_{us}$, $\delta t_{RX,0}$, being a constant delay upon reception.

To introduce this delay upon emission, the control module 20 may generate a reference transmission control signal $S_{TX,0}$ (based on a predetermined transmission sequence stored in a memory of the control module, for instance), when a probing (or measurement) pulse is to be tracked, this signal being then delayed in a controlled manner, using a controllable delay 23, to produce the transmission control signal $S_{TX}$ sent to the U/S front end 40. The temporal shift upon reception $\delta t_{RX}$ may be obtained using a controllable sequencer 22, selecting the appropriate series of values in a digitalized signal outputted by the amplifier and ADC 42, using a shift register or another kind of digital buffer, for instance. And a correction module 21 may determine the variable delay d/vus, from the digitalized signal outputted by the signal conditioning module 32 (digitalized signal which is representative of the signal outputted by the displacement sensor 11). In the embodiment of FIGS. 6 to 8, the displacement d of the transducer 6 is its displacement relative to the probe's casing 3.

Regarding the mechanical vibrations exerted on the body of the subject in the guidance mode, to probe the region facing the probe, it may be noted that, in an alternative embodiment, the vibrator may be controlled in a hybrid manner, so as to deliver transient pulses (namely the probing pulses PRB mentioned above) as well as a periodic mechanical vibration PMV. The displacement d of the tip 4 is represented over time t in FIG. 13, for an example of such a hybrid probing.

Figure 13:
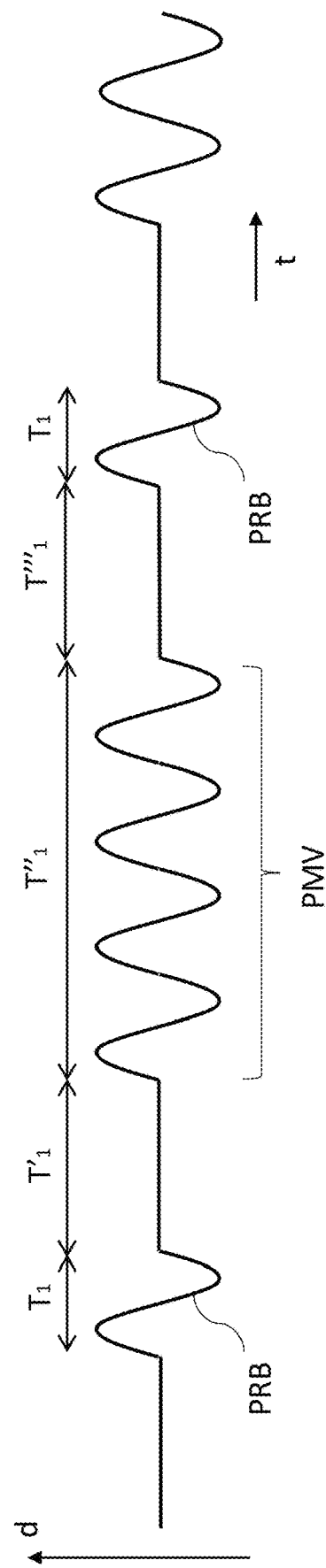
FIG. 13 schematically represents the displacement over time of a tip of the elastography device when the device is in the guidance mode, according to alternative embodiment.

For such a hybrid probing/guidance, each probing pulse PRB is followed by a time lapse $T_1'$ with substantially no displacement of the tip 4 (a downtime), and then by a periodic mechanical vibration PMV, comprising of a same vibration pattern repeated several times successively over time, with substantially no downtime of the vibrator during the periodic mechanical vibration PMV. The periodic mechanical vibration PMV may comprise at least 3, or even at least 5 occurrences of the vibration pattern, which is for instance one period of a sinusoid. As represented in FIG. 13, the periodic mechanical vibration comprises of 4 occurrences of the vibration pattern (4 successive periods of a sinusoid, in this case). The duration of the periodic mechanical vibration PMV is $T_1''$. The periodic mechanical vibration is followed by a downtime of duration $T_1'''$ before any new probing pulse is delivered.

The duration $T_1'$ of the post-probing pulse downtime may be higher than $1/f_{c,1}$, or higher than $T_1$ or even higher than twice $T_1$, and the same for $T_1'''$.

Probing the probed region 80 both with a transient mechanical pulse (the probing pulse PRB), and with the periodic mechanical vibration enables to detect that the probing axis z is close to an edge of an organ to be characterized. (close, from a lateral point of view; i.e.: passes close to this edge of the organ).

Figure 3:
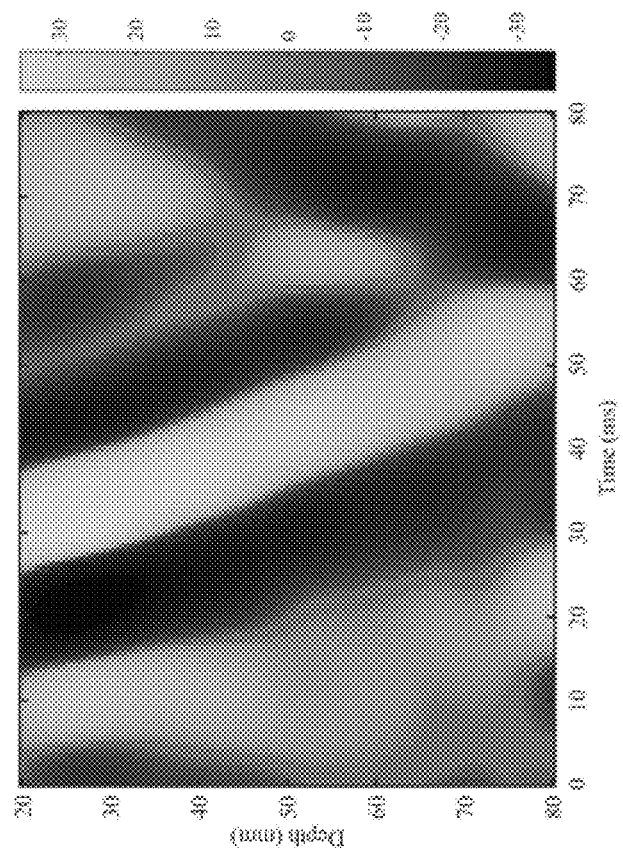
FIG. 3 shows an elastogram obtained in the same conditions as in FIG. 2 expect that the mechanical vibration is a transient mechanical pulse.
Figure 2:
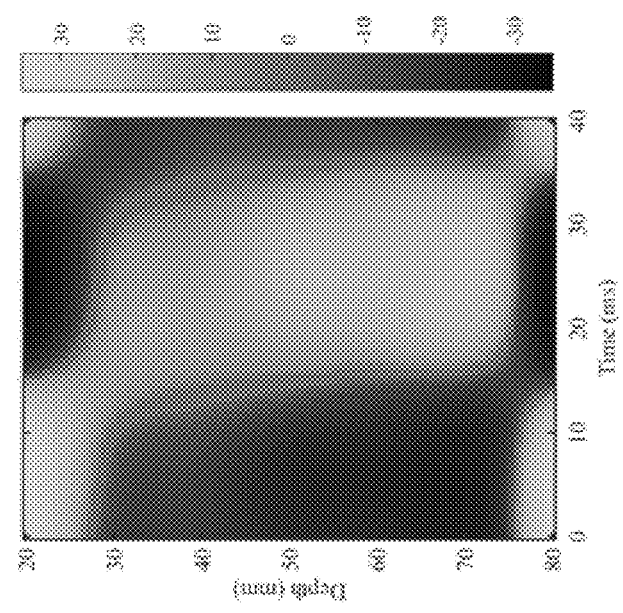
FIG. 2 shows an elastogram obtained when exerting a sinusoidal mechanical vibration (lasting for several periods) on an elastic medium.
Figure 5:
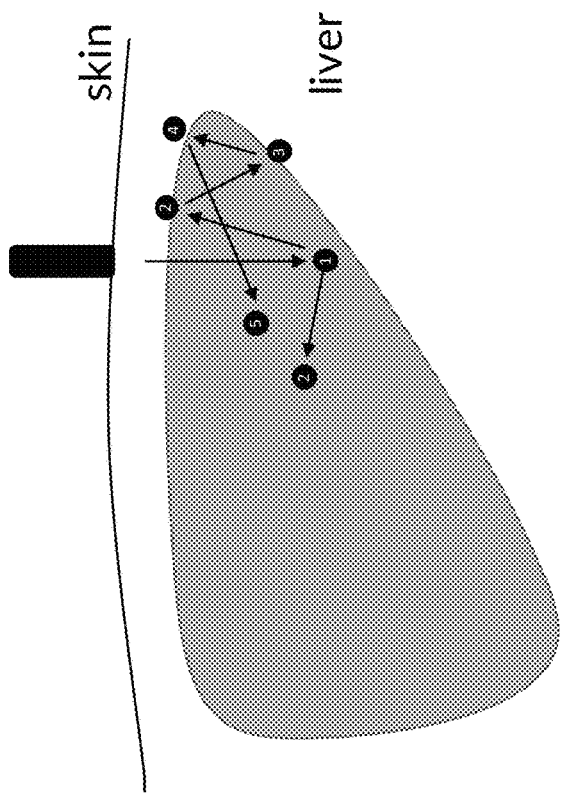
FIGS. 4 and 5 schematically illustrate the influence of organ boundaries when probing an organ respectively with a transient pulse and with an harmonic mechanical vibration.
Figure 4:
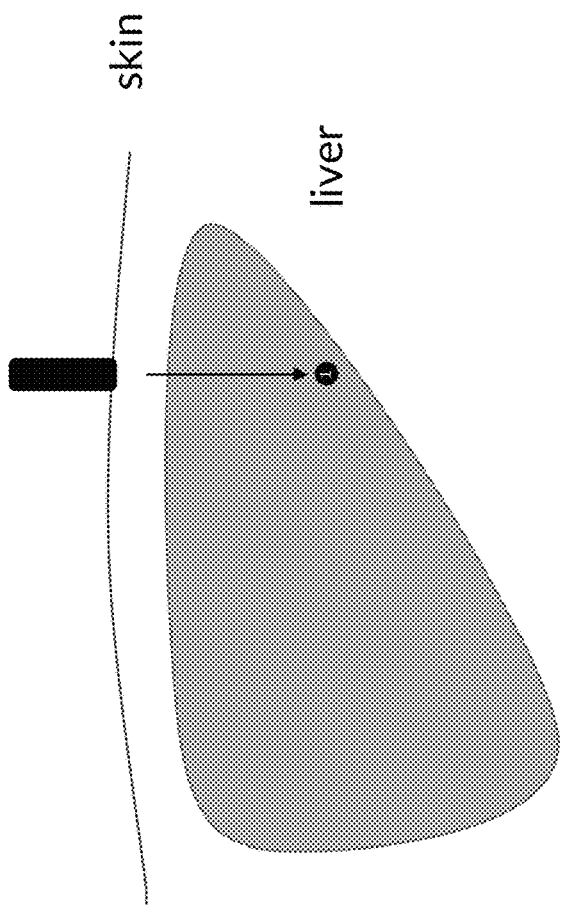

Indeed, as explained in the section "summary", with reference to FIGS. 2 and 3, when probing a medium with a periodic (e.g. harmonic) vibration, the proximity of a wall, edge, or medium discontinuity often disturb the propagation of the vibration, favorizing stationary waves patterns. On the contrary, the propagation of transient mechanical pulses is less disturbed by such edges. So, the fact that a transient mechanical pulse can propagate through the probed region, while a periodic vibration does not (or at least propagates with a very strong distortion), indicates that the probing axis z probably passes close to an edge of the organ to be characterized.

In this alternative embodiment, when in the guidance mode, the electronic unit controls the ultrasound transducer 6 to emit a sequence of ultrasound pulses and to acquire echo signals received in response, to track how the probing pulses, and the periodic mechanical vibration propagates through the probed region of the body of the subject.

The electronic unit then determines a periodic-vibration propagation quality level, from at least some of these echo signals, in addition to the (transient) propagation quality indicator Q described above.

The periodic-vibration propagation quality level may be specified whether the elastogram associated to this vibration comprises of well-defined diagonal bands, or not. It may also specify whether a phase delay of this vibration varies substantially linearly, and smoothly with depth, or not.

Then the electronic unit determines an edge-proximity indicator, based on a comparison of the periodic-vibration propagation quality level with the propagation quality indicator Q, and transmits this edge-proximity indicator (communicates it to an operator of the elastography device). The edge-proximity indicator may be a binary indicator, for instance, switching from off to on when a difference between the propagation quality indicator Q and the periodic-vibration propagation quality level becomes higher than a given threshold.

We claim:

1. An elastography device comprising:
a probe that comprises: a protruding part to be applied against the body of a subject, a low frequency vibrator arranged to move the protruding part of the probe, at least one ultrasound emitter and one ultrasound receiver, and
an electronic unit comprising electronic circuitry adapted to alternatively control the elastography device so that it operates (a) in a guidance mode to determine whether the probe is correctly positioned in front of a region of the body to be probed to carry out a measurement of a mechanical property of the probed region and (b) in a measurement mode to carry out said measurement, the electronic circuitry being adapted to execute the following procedure:
during the guidance mode,
the electronic unit controls the low frequency vibrator to deliver to the body of the subject, successively and repeatedly, a plurality of probing pulses, each of the plurality of probing pulses being a transient, low frequency mechanical pulse,
for each of the plurality of probing pulses,
the electronic unit controls the ultrasound emitter to emit a first sequence of ultrasound pulses, and acquires first echo signals received in response by the ultrasound receiver to track how said each of the plurality of probing pulses propagates through the probed region of the body of the subject, located in front of the protruding part of the probe,
the electronic unit determines, from at least some of said first echo signals, a propagation quality indicator representative of an aptitude of the probed region to transmit said each of the plurality of probing pulses and representative of a homogeneity of the probed region with respect to the propagation of said each of the plurality of probing pulses,
the electronic unit controls the elastography device to transmit guidance information, the guidance information being based on the propagation quality indicator,
during the measurement mode,
the electronic unit controls the low frequency vibrator to deliver to the probed region a measurement pulse, the measurement pulse being a transient low frequency mechanical pulse having an amplitude higher than an amplitude of each of the plurality of probing pulses,
the electronic unit controls the ultrasound emitter to emit a second sequence of ultrasound pulses, and acquires second echo signals received in response by the ultrasound receiver to track how the measurement pulse propagates through the probed region, and
the electronic unit determines, from at least some of said second echo signals, said mechanical property, said mechanical property being related to low frequency elastic wave propagation.

2. The elastography device of claim 1, wherein the electronic unit is configured to control the vibrator so that, in said guidance mode, for at least some of the plurality of probing pulses, a central frequency of each of said at least some of the plurality of probing pulses is lower than a central frequency of the measurement pulse delivered in said measurement mode.

3. The elastography device of claim 1, configured for characterizing liver, wherein the electronic unit is configured to control the vibrator so that, in said guidance mode, for at least some of the plurality of probing pulses, a central frequency of each of said at least some of the plurality of probing pulses is between 20 Hz and 45 Hz while, in said measurement mode, a central frequency of the measurement pulse is between 50 Hz and 200 Hz.

4. The elastography device of claim 1, configured for characterizing spleen, wherein the electronic unit is configured to control the vibrator so that, in said guidance mode, for at least some of the plurality of probing pulses, a central frequency of each of said at least some of the plurality of probing pulses is between 20 Hz and 90 Hz while, in said measurement mode, a central frequency of the measurement pulse is between 100 Hz and 200 Hz.

5. The elastography device of claim 1, wherein the electronic unit is configured to control the vibrator so that, in said guidance mode, for at least some of the plurality of probing pulses, an amplitude of displacement of the protruding part of the probe is at least 20% lower than an amplitude of displacement of the protruding part during the measurement pulse delivered in said measurement mode.

6. The elastography device of claim 1, wherein the electronic unit is configured to control the ultrasound emitter so that, in said guidance mode, for at least some of the plurality of probing pulses, a repetition rate with which the ultrasound pulses are emitted in said first sequence of ultrasound pulses, to track how each of said at least some of the plurality of probing pulses propagates, is lower than a repetition rate of the ultrasound pulses that are emitted in said second sequence of ultrasound pulses during the measurement mode to track how the measurement pulse propagates.

7. The elastography device of claim 1, wherein the electronic unit is configured to control the vibrator so that, in said guidance mode, the plurality of probing pulses are delivered with a rate of more than one pulses per second.

8. The elastography device of claim 1, wherein the electronic unit is configured so that, in said guidance mode, for at least some of the plurality of probing pulses, a time lag between the transmission of each of said at least some of the plurality of probing pulses to the body of the subject, and a transmission of the corresponding guidance information, is below 0.5 second and/or is below a repetition period with which said at least some of the plurality of probing pulses are repeated.

9. The elastography device of claim 1, wherein the electronic unit is configured so that, in said guidance mode, for each of the plurality of probing pulses, the electronic unit determines tissue strain data, representative of tissue strain within the probed region as a function of time and as a function of depth within the probed region, the tissue strain data being determined from at least some of the echo signals acquired to track how said each of the plurality of probing pulses propagates through the probed region.

10. The elastography device of claim 9, wherein, in said guidance mode, the electronic unit determines the propagation quality indicator based on the tissue strain data.

11. The elastography device of claim 10, wherein, in said guidance mode, for each of the plurality of probing pulses:
the electronic unit determines a probing pulse time of flight, as a function of depth within the probed region, the probing pulse time of flight being determined from the tissue strain data, and
the electronic unit determines the propagation quality indicator so that it specifies whether the probing pulse time of flight varies linearly and smoothly and with depth, or not.

12. The elastography device of claim 9, wherein, in said guidance mode, the electronic unit is configured to compute averaged tissue strain data by averaging the tissue strain data corresponding respectively to several of the plurality of probing pulses.

13. The elastography device of claim 12, wherein, in said guidance mode, the electronic unit is configured to control a display device to display an averaged elastogram representing the averaged tissue strain data as a function of time and depth.

14. The elastography device of claim 1, wherein the electronic unit is configured so that, in said measurement mode:
electronic unit controls the vibrator to deliver to the body of the subject, in addition to said measurement pulse, one or more subsequent, additional measurement pulses, each being a transient low frequency mechanical pulse,
for each measurement pulse, the electronic unit determines tissue strain data within the probed region, from echo signals acquired to track how each measurement pulse propagates through the probed region,
the electronic unit determines said mechanical property related to low frequency elastic wave propagation by averaging, taking into account the tissue strain data associated respectively to the different measurement pulses delivered to the body of the subject.

15. The elastography device of claim 1, wherein the electronic unit is configured to adjust a central frequency of the measurement pulse to be delivered to the body of the subject, based on a property of the probed region of the body of the subject probed by at least one of the plurality of probing pulses.

16. The elastography device of claim 15, wherein said property is representative of an attenuation underwent by said at least one of the plurality of probing pulses during its propagation within said probed region, and wherein the electronic unit is configured to adjust the central frequency of the measurement pulse so that it is all the higher as the attenuation in the region is high.

17. The elastography device of claim 1, wherein the electronic unit is configured to:
control the vibrator so that, during the guidance mode, at least some of the plurality of probing pulses are each followed:
by a time lapse with substantially no displacement of the protruding part of the probe,
and then by a periodic mechanical vibration, comprising of a same vibration pattern repeated several times successively over time, with substantially no downtime of the vibrator during the periodic mechanical vibration,
emit a third sequence of ultrasound pulses and to acquire third echo signals received in response, to track how the periodic mechanical vibration propagates through the probed region of the body of the subject, located in front of the protruding part of the probe, and to determine a periodic-vibration propagation quality level, from at least some of these echo signals, and
determine an edge-proximity indicator based on a comparison of the periodic-vibration propagation quality level with the propagation quality indicator, and to transmit the edge-proximity indicator.

18. An elastography method,
implemented by an elastography device that includes a probe including a protruding part to be applied against the body of a subject, a low frequency vibrator arranged to move the protruding part of the probe, at least one ultrasound emitter and one ultrasound receiver; and an electronic unit, comprising electronic circuitry adapted to alternatively control the elastography device so that it operates (a) in a guidance mode to determine whether the probe is correctly positioned in front of a region of the body to be probed to carry out a measurement of a mechanical property of the probed region and (b) in a measurement mode to carry out said measurement
the method comprising:
carrying out the guidance mode, the guidance mode including:
controlling, by the electronic unit, the vibrator to deliver to the body of the subject, successively and repeatedly, a plurality of probing pulses, each of the plurality of probing pulses being a transient, low frequency mechanical pulse,
for each of the plurality of probing pulses,
controlling, by the electronic unit, the ultrasound emitter to emit a first sequence of ultrasound pulses, and acquiring, by the ultrasound receiver, first echo signals to track how said each of the plurality of probing pulses propagates through the probed region of the body of the subject located in front of the protruding part of the probe,
determining, by the electronic unit, from at least some of said first echo signals, a propagation quality indicator representative of an aptitude of the probed region to transmit said each of the plurality of probing pulses and representative of a homogeneity of the probed region with respect to the propagation of said each of the plurality of probing pulses,
transmitting guidance information, the guidance information being based on the propagation quality indicator, and then,
carrying out the measurement mode, the measurement mode including:
controlling, by the electronic unit, the vibrator, to deliver to the body of the subject a measurement pulse, the measurement pulse being a transient low frequency mechanical pulse having an amplitude higher than an amplitude of each of the plurality of probing pulses,
controlling, by the electronic unit, the ultrasound emitter to emit a second sequence of ultrasound pulses, and acquiring, by the ultrasound receiver, second echo signals to track how the measurement pulse propagates through the probed region of the body of the subject located in front of the protruding part of the probe, and
determining, by the electronic unit, from at least some of said second echo signals, the mechanical property of said region of the body of the subject, related to low frequency elastic wave propagation.

\* \* \* \* \*